US012773162B2

(12) United States Patent
Moore et al.

(10) Patent No.: US 12,773,162 B2
(45) Date of Patent: Oct. 27, 2026

(54) SYSTEMS FOR DETERMINING MEDICATION-ADJUSTED CLINICAL EFFECTS

(71) Applicant: Boston Scientific Neuromodulation Corporation, Valencia, CA (US)

(72) Inventors: Lisa Denise Moore, Glendale, CA (US); Michael A. Moffitt, Solon, OH (US); Leon Mauricio Juarez Paz, Berlin (DE); Stephen Carcieri, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 434 days.

(21) Appl. No.: 18/240,042

(22) Filed: Aug. 30, 2023

(65) Prior Publication Data

US 2024/0065620 A1 Feb. 29, 2024

Related U.S. Application Data

(60) Provisional application No. 63/402,153, filed on Aug. 30, 2022.

(51) Int. Cl.

*A61B 5/00* (2006.01)
*A61N 1/36* (2006.01)
*A61N 1/365* (2006.01)

(52) U.S. Cl.

CPC .......... *A61B 5/4848* (2013.01); *A61B 5/4839* (2013.01); *A61B 5/7221* (2013.01); (Continued)

(58) Field of Classification Search

None

See application file for complete search history.

(56) References Cited

U.S. PATENT DOCUMENTS 8,934,963 B1 * 1/2015 Farazi .................. A61B 5/4848 600/517
10,261,811 B2 4/2019 Morelli et al.
(Continued)

FOREIGN PATENT DOCUMENTS

WO WO-2024049897 A1 3/2024

OTHER PUBLICATIONS

"European Application Serial No. 23773059.3, Response to Communication pursuant to Rules 161 and 162 EPC filed Sep. 24, 2025", 8 pgs.

(Continued)

*Primary Examiner* — Benjamin J Klein
*Assistant Examiner* — Willow Grace Welch
(74) *Attorney, Agent, or Firm* — Schwegman Lundberg & Woessner, P.A.

(57) ABSTRACT

A system may include at least one medical device and a processing system. The medical device may be configured to treat a condition by delivering a therapy to a patient. The therapy is at least partially defined using a parameter set. The processing system may be configured for use to acquire clinical effect data (CED) for the condition, acquire a medication state of medication administered to treat the condition, adjust the CED based on the medication state to provide medication-adjusted CED, and identify an adjusted parameter set for the at least one medical device to deliver the therapy based on the medication-adjusted CED. The adjusted parameter set may be communicated to a clinician (or patient or other user) as a suggestion or may be automatically implemented to update the therapy.

20 Claims, 12 Drawing Sheets

(52) U.S. Cl.
CPC ..... *A61N 1/36067* (2013.01); *A61N 1/36071* (2013.01); *A61N 1/36132* (2013.01); *A61N 1/36139* (2013.01); *A61N 1/36564* (2013.01)

(56) References Cited

U.S. PATENT DOCUMENTS

| | | | | |
|---|---|---|---|---|
| 10,265,528 | B2 | 4/2019 | Carcieri et al. | |
| 10,357,657 | B2 | 7/2019 | Moffitt et al. | |
| 10,603,498 | B2 | 3/2020 | Blum et al. | |
| 11,344,732 | B2 * | 5/2022 | Moffitt | A61N 1/3614 |
| 2003/0149457 | A1 * | 8/2003 | Tcheng | A61N 1/36135 607/48 |
| 2004/0249422 | A1 * | 12/2004 | Gliner | A61N 1/0534 607/45 |
| 2008/0039904 | A1 * | 2/2008 | Bulkes | A61N 1/37512 607/116 |
| 2014/0257047 | A1 * | 9/2014 | Sillay | H04L 63/10 600/595 |
| 2014/0350623 | A1 * | 11/2014 | Fischer | A61N 1/39622 607/11 |
| 2018/0104500 | A1 | 4/2018 | Blum et al. | |
| 2018/0192943 | A1 * | 7/2018 | Annoni | A61N 1/37211 |
| 2022/0016415 | A1 | 1/2022 | Arlotti et al. | |
| 2022/0257950 | A1 | 8/2022 | Moore et al. | |
| 2022/0266023 | A1 * | 8/2022 | Litvak | A61B 5/4064 |
| 2022/0355114 | A1 | 11/2022 | Moore et al. | |
| 2022/0355115 | A1 | 11/2022 | Moore et al. | |
| 2023/0141183 | A1 | 5/2023 | Moore et al. | |

OTHER PUBLICATIONS

"International Application Serial No. PCT/US2023/031526, International Preliminary Report on Patentability mailed Mar. 13, 2025", 10 pgs.

"International Application Serial No. PCT/US2023/031526, International Search Report mailed Dec. 8, 2023", 4 pgs.

"International Application Serial No. PCT/US2023/031526, Written Opinion mailed Dec. 8, 2023", 8 pgs.

"Australian Application Serial No. 2023336028, First Examination Report mailed Apr. 13, 2026", 4 pgs.

* cited by examiner

SYSTEMS FOR DETERMINING MEDICATION-ADJUSTED CLINICAL EFFECTS

CLAIM OF PRIORITY

This application claims the benefit of U.S. Provisional Application No. 63/402,153, filed on Aug. 30, 2022, which is hereby incorporated by reference in its entirety.

TECHNICAL FIELD

This document relates generally to medical systems, and more particularly, but not by way of limitation, to systems, devices, and methods for determining medication-adjusted clinical effects, thereby accounting for medication state to improve clinical effect data (CED) capture and programming.

BACKGROUND

Medical devices may include therapy-delivery devices configured to deliver a therapy to a patient and/or monitors configured to monitor a patient condition via user input and/or sensor(s). For example, therapy-delivery devices for ambulatory patients may include wearable devices and implantable devices, and further may include, but are not limited to, stimulators (such as electrical, thermal, or mechanical stimulators) and drug delivery devices (such as an insulin pump). An example of a wearable device includes, but is not limited to, transcutaneous electrical neural stimulators (TENS), such as may be attached to glasses, an article of clothing, or a patch configured to be adhered to skin. Implantable stimulation devices may deliver electrical stimuli to treat various biological disorders, such as pacemakers to treat cardiac arrhythmia, defibrillators to treat cardiac fibrillation, heart failure cardiac resynchronization therapy devices, cochlear stimulators to treat deafness, retinal stimulators to treat blindness, muscle stimulators to produce coordinated limb movement, spinal cord stimulators (SCS) to treat chronic pain, cortical and Deep Brain Stimulators (DBS) to treat motor and psychological disorders, Peripheral Nerve Stimulation (PNS), Functional Electrical Stimulation (FES), and other neural stimulators to treat urinary incontinence, sleep apnea, shoulder subluxation, etc.

A therapy device may be configured to treat a condition. Thus, by way of example and not limitation, a DBS system may be configured to treat motor disorders such as, but not limited to, tremor, bradykinesia, and dyskinesia associated with Parkinson's Disease (PD). In another nonlimiting example, a stimulation device, such as neurostimulation device (e.g., DBS, SCS, PNS or TENS), may be configured to treat pain. In another nonlimiting example, a device, such as a myocardial stimulator and/or neurostimulator, may be configured to treat cardiovascular condition. Settings of the therapy device may be programmed based on observed clinical effects so that the therapy provides desirable intended effects (e.g., reduced tremor, bradykinesia, and dyskinesia for a PD therapy, desirable pain relief or paresthesia coverage for a pain therapy, desirable blood pressure and/rhythms for a cardiovascular therapy) while avoiding undesirable side effects.

SUMMARY

An example (e.g., "Example 1") of a system may include at least one medical device and a processing system. More than one medical device may be used such as a stimulator and a pump, by way of example and not limitation. The at least one medical device may be configured to treat a condition by delivering a therapy that is at least partially defined using a parameter set. The processing system may be configured for use to acquire clinical effect data (CED) for the condition, acquire a medication state of medication administered to treat the condition, adjust the CED based on the medication state to provide medication-adjusted CED, and identify an adjusted parameter set for the at least one medical device to deliver the therapy based on the medication-adjusted CED. The adjusted parameter set may be communicated to a user (e.g., clinician, patient or caregiver) as a suggestion or may be automatically implemented to update the therapy.

In Example 2, the subject matter of Example 1 may optionally be configured such that the adjusted parameter set is identified based on a comparison of a current medication-adjusted CED to a previous medication-adjusted CED.

In Example 3, the subject matter of any one or more of Examples 1-2 may optionally be configured such that the processing system is configured to acquire the medication state by estimating the medication state.

In Example 4, the subject matter of Example 3 may optionally be configured such that the medication state is estimated based on at least one of: a medication schedule; the medication, the dose of the medication, and user input indicating a time when medication is administered; a characteristic shift in the treated condition, wherein the characteristic shift is determined using at least one of a sensor of the treated condition or a user input indicative of the treated condition; or at least one sensor configured to detect a characteristic shift in a physiological parameter.

In Example 5, the subject matter of any one or more of Examples 3-4 may optionally be configured such that the medication state is estimated using a neural sensor configured to detect a characteristic change in neural activity.

In Example 6, the subject matter of any one or more of Examples 1-5 may optionally be configured to further include at least one sensor configured to detect the medication state by detecting a concentration of the medication.

In Example 7, the subject matter of any one or more of Examples 1-6 may optionally be configured such that the medication state of medication includes medication states for more than one medicine, alone or in combination.

In Example 8, the subject matter of any one or more of Examples 1-7 may optionally be configured such that the at least one medical device includes a deep brain stimulator (DBS) configured to deliver an electrical therapy to treat movement disorders (such as but not limited to Parkinson's Disease (PD)). The CED may include data indicative of movement (such as but not limited to, tremor, bradykinesia, dyskinesia gait, rigidity, and the like), The system may further include an accelerometer configured to detect motion to determine the CED.

In Example 9, the subject matter of any one or more of Examples 1-8 may optionally be configured such that the therapy includes an electrical therapy, and the adjusted parameter set includes an adjustment to at least one of: a pulse amplitude; a pulse width; a pulse frequency; a pulse train duration; a pulse-to-pulse duty cycle; a pulse train to pulse train duty cycle; a stimulation schedule; active electrodes; or electrode fractionalization.

In Example 10, the subject matter of any one or more of Examples 1-9 may optionally be configured such that the at least one medical device is capable delivering the therapy within a therapy space defined by different parameters sets that define values for a plurality of therapy parameters. The different parameter sets may include a first group for calibration and a second group. The at least one medical device may be configured to capture CED for the first group within the therapy space by delivering the therapy using each of the different parameter sets within the first group, wherein the system is configured to capture the CED for each of the different parameter sets, adjust the captured CED based on the medication state to provide medication-adjusted captured CED for each of the different parameter sets in the first group.

In Example 11, the subject matter of Example 10 may optionally be configured such that the processing system is configured to determine a CED map using the captured CED for the first group to estimate medication-adjusted CED for different parameter sets within the second group.

In Example 12, the subject matter of Example 11 may optionally be configured such that the processing system is configured to use data from other patients to estimate medication-adjusted CED for different parameter sets within the second group.

In Example 13, the subject matter of any one or more of Examples 11-12 may optionally be configured such that the processing system is configured to associate the captured and estimated CED with an acceptable error based on an anticipated error rate, capture CED for at least one parameter set which was previously estimated in the second group and determine the captured CED is outside of the acceptable error and respond by updating the CED map.

In Example 14, the subject matter of any one or more of Examples 1-13 may optionally be configured such that the acquired CED includes previously collected data retrieved from storage, and the medication state is acquired using a medication schedule, user-inputted data indicating a time when medication was administered, or sensor data.

In Example 15, the subject matter of any one or more of Examples 1-14 may optionally be configured such that the medication state is a dimension in a CED vector or matrix used by an optimizer rather than predicting a clinical effect.

Example 16 includes subject matter (such as a method, means for performing acts, machine readable medium including instructions that when performed by a machine cause the machine to perform acts, or an apparatus to perform). The subject matter may include using a medical device configured to treat a condition by delivering a therapy that is at least partially defined using a parameter set. A processing system may be used to acquire clinical effect data (CED) for the condition, acquire a medication state of medication administered to treat the condition, adjust the CED based on the medication state to provide medication-adjusted CED, and identify an adjusted parameter set for the medical device to deliver the therapy based on the medication-adjusted CED. The adjusted parameter set may be communicated to a user (e.g., clinician, patient or caregiver), and or may be automatically implemented.

In Example 17, the subject matter of Example 16 may optionally be configured such that the adjusted parameter set is identified based on a comparison of a current medication-adjusted CED to a previous medication-adjusted CED.

In Example 18, the subject matter of any one or more of Examples 16-17 may optionally be configured to further include determining the medication state for at least one medicine by using at least one sensor to determine the medication state by detecting a concentration of the medication in the patient, or estimating the medication state. The medication state may be estimated based on at least one of: a medication schedule; the medication, the dose of the medication, and user input indicating a time when medication is administered; a characteristic shift in the treated condition, wherein the characteristic shift is determined using at least one of a sensor of the treated condition or a user input indicative of the treated condition; or at least one sensor configured to detect a characteristic shift in a physiological parameter.

In Example 19, the subject matter of Example 18 may optionally be configured such that the therapy includes deep brain stimulation (DBS) to treat Parkinson's Disease (PD). An accelerometer may be used to detect the CED, wherein the CED includes data indicative of movement disorder.

In Example 20, the subject matter of Example 18 may optionally be configured such that the therapy includes a neurostimulation therapy to treat pain. At least one of patient feedback or sensed data regarding pain may be used to detect the CED for the neurostimulation therapy.

In Example 21, the subject matter of Example 18 may optionally be configured such that the therapy includes electrical stimulation for a cardiovascular therapy. At least one of blood pressure or cardiac activity may be used to detect the CED for the cardiovascular therapy.

In Example 22, the subject matter of any one or more of Examples 16-21 may optionally be configured such that the therapy includes an electrical therapy. The adjusted parameter set may include an adjustment to at least one of: a pulse amplitude; a pulse width; a pulse frequency; a pulse train duration; a pulse-to-pulse duty cycle; a pulse train to pulse train duty cycle; a stimulation schedule; active electrodes; or electrode fractionalization.

In Example 23, the subject matter of any one or more of Examples 16-22 may optionally be configured such that the acquired CED includes previously collected data retrieved from storage, and the medication state is acquired using a medication schedule, user-inputted data indicating a time when medication was administered, or sensor data.

In Example 24, the subject matter of any one or more of Examples 16-23 may optionally be configured such that the medication state is a dimension in a CED vector or matrix used by an optimizer to determine the adjusted parameter set.

In Example 25, the subject matter of any one or more of Examples 16-24 may optionally be configured such that the therapy is delivered within a therapy space defined by different parameters sets that define values for a plurality of therapy parameters. The different parameter sets may include a first group for calibration and a second group. The medical device may be used to capture CED for the first group within the therapy space by delivering the therapy using each of the different parameter sets within the first group, capturing the CED for each of the different parameter sets, and adjusting the captured CED based on the medication state to provide medication-adjusted captured CED for each of the different parameter sets in the first group.

In Example 26, the subject matter of Example 25 may optionally be configured to further include using the processing system to determine a prediction map using the captured CED for the first group to estimate medication-adjusted CED for different parameter sets within the second group.

In Example 27, the subject matter of Example 18 may optionally be configured to further include using data from other patients to estimate medication-adjusted CED for different parameter sets within the second group.

In Example 28, the subject matter of any one or more of Examples 26-27 may optionally be configured to further include using the processing system to associate the captured and estimated CED with an acceptable error based on an anticipated error rate, capture CED for at least one parameter set which was previously estimated in the second group and determine the captured CED is outside of the acceptable error and respond by updating the prediction map.

In Example 29, the subject matter of Example 28 may optionally be configured to further include assigning a confidence level to parameter sets within the second group based on an accuracy of estimation for the captured CED for the at least one parameter set in the second group, and testing other parameter sets in the second group based in the assigned confidence level.

In Example 30, the subject matter of any one or more of Examples 16-29 may optionally be configured such that the adjusted parameter set maintains the acquired CED within a set range by accounting for fluctuations in the medication state attributable to an absorption rate and clearance rate of the administered medicine.

In Example 31, the subject matter of any one or more of Examples 16-30 may optionally be configured to further include using the processing system to gradually ramp from the parameter set used to deliver the therapy to the adjusted parameter set.

In Example 32, the subject matter of any one or more of Examples 16-31 may optionally be configured to further include creating CED maps at a plurality of times to map the medication-adjusted CED to the parameter set at each of the plurality of times, and displaying the CED maps to a clinician or a patient.

Example 33 includes subject matter (such as a method, means for performing acts, machine readable medium including instructions that when performed by a machine cause the machine to perform acts, or an apparatus to perform). The subject matter may include using a medical device configured to treat a condition by delivering a therapy, wherein the therapy is at least partially defined using a parameter set. A processing system may be used to acquire first clinical effect data (CED) for the condition at a first medication state, acquire second CED for the condition at a second medication state, estimate third CED for the condition at a third medication state using the first CED and the second CED, and identify an adjusted parameter set for the medical device to deliver the therapy based on the third CED. The adjusted parameter set may be communicated to a user (e.g., clinician, patient or caregiver) as a suggestion or may be automatically implemented.

In Example 34, the subject matter of Example 33 may optionally be configured such that the acquired first CED includes CED for tested parameter sets and estimated CED for non-tested parameters.

In Example 35, the subject matter of any one or more of Examples 16-30 may optionally be configured such that the processing system is configured to verify the estimated third CED by testing at least some parameter sets.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to “an”, “one”, or “various” embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to medical systems used in the analysis of CED which may be captured or otherwise acquired by the medical systems. The medical systems may include therapy-delivery devices and/or monitors to monitor a patient condition. The CED may be used to program a therapy-delivery device such as an electrical therapy-delivery device used in treating the patient condition. DBS to treat movement disorders is discussed below as a specific example of a therapy-delivery device. Other examples include, but are not limited to, SCS to treat pain and a cardiovascular therapy-delivery device, such as a pacemaker or defibrillator. TENS, PNS, FES and other neural stimulators also may be programmed to desirable settings using CED analysis. The present subject may be used with any clinical effects that may be modulated by the patient's medication state.

Figure 1:
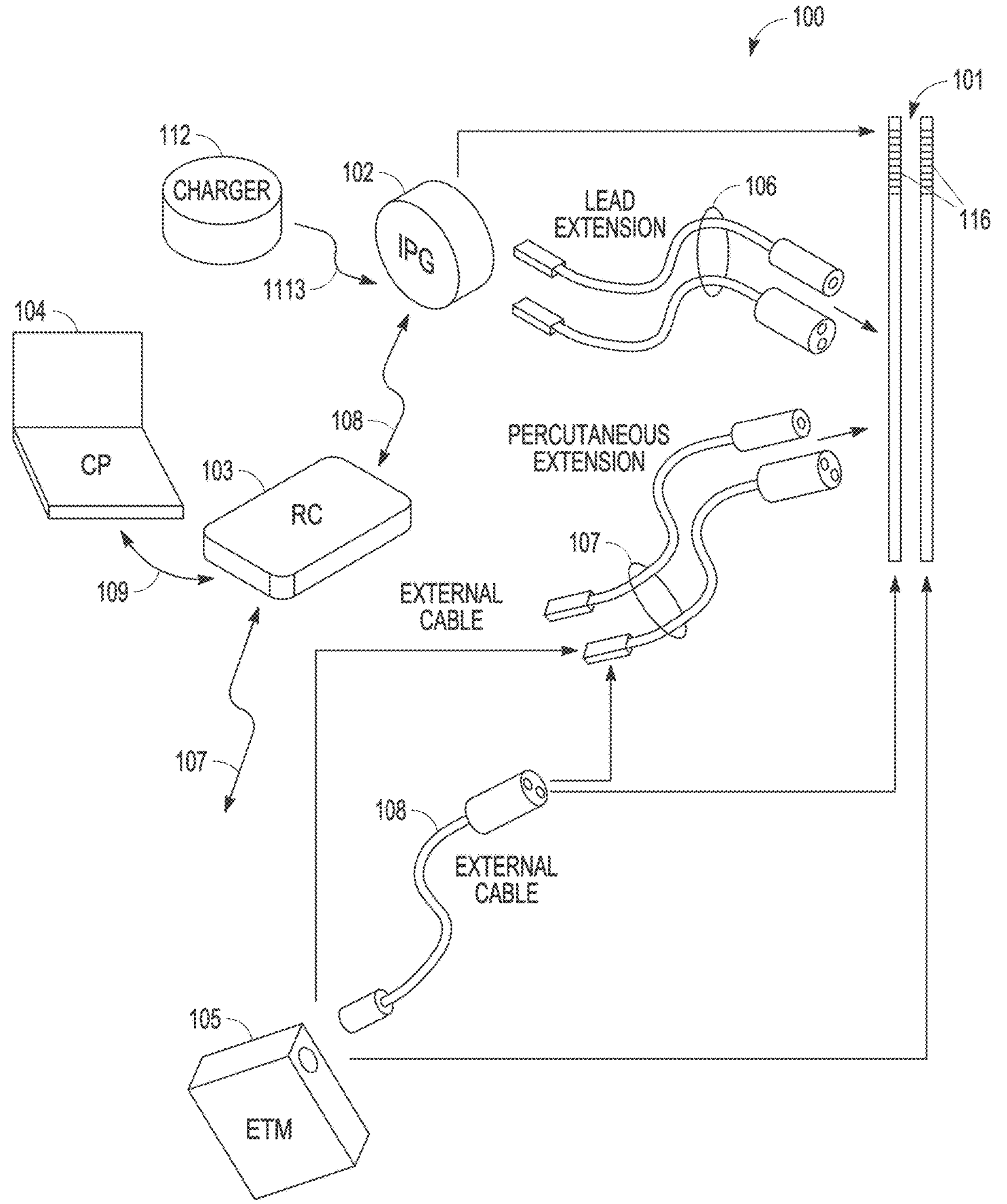
FIG. 1 illustrates, by way of example and not limitation, an electrical stimulation system, which may be used to deliver DBS.

FIG. 1 illustrates, by way of example and not limitation, an electrical stimulation system 100, which may be used to deliver DBS. The electrical stimulation system 100 may generally include a one or more (illustrated as two) of implantable neuromodulation leads 101, a waveform generator such as an implantable pulse generator (IPG) 102, an external remote controller (RC) 103, a clinician programmer (CP) 104, and an external trial modulator (ETM) 105. The IPG 102 may be physically connected via one or more percutaneous lead extensions 106 to the neuromodulation lead(s) 101, which carry a plurality of electrodes 116. The electrodes, when implanted in a patient, form an electrode arrangement. As illustrated, the neuromodulation leads 101 may be percutaneous leads with the electrodes arranged in-line along the neuromodulation leads or about a circumference of the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 102 includes pulse generation circuitry that delivers electrical modulation energy in the form of a pulsed electrical waveform (i.e., a temporal series of electrical pulses) to the electrodes in accordance with a set of modulation parameters.

The ETM 105 may also be physically connected via the percutaneous lead extensions 107 and external cable 108 to the neuromodulation lead(s) 101. The ETM 105 may have similar pulse generation circuitry as the IPG 102 to deliver electrical modulation energy to the electrodes in accordance with a set of modulation parameters. The ETM 105 is a non-implantable device that may be used on a trial basis after the neuromodulation leads 101 have been implanted and prior to implantation of the IPG 102, to test the responsiveness of the modulation that is to be provided. Functions described herein with respect to the IPG 102 can likewise be performed with respect to the ETM 105.

The RC 103 may be used to telemetrically control the ETM 105 via a bi-directional RF communications link 109. The RC 103 may be used to telemetrically control the IPG 102 via a bi-directional RF communications link 110. Such control allows the IPG 102 to be turned on or off and to be programmed with different modulation parameter sets. The IPG 102 may also be operated to modify the programmed modulation parameters to actively control the characteristics of the electrical modulation energy output by the IPG 102. A clinician may use the CP 104 to program modulation parameters into the IPG 102 and ETM 105 in the operating room and in follow-up sessions.

The CP 104 may indirectly communicate with the IPG 102 or ETM 105, through the RC 103, via an IR communications link 111 or another link. The CP 104 may directly communicate with the IPG 102 or ETM 105 via an RF communications link or other link (not shown). The clinician detailed modulation parameters provided by the CP 104 may also be used to program the RC 103, so that the modulation parameters can be subsequently modified by operation of the RC 103 in a stand-alone mode (i.e., without the assistance of the CP 104). Various devices may function as the CP 104. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 104. Alternatively, such programming methodologies can be performed using firmware or hardware. In any event, the CP 104 may actively control the characteristics of the electrical modulation generated by the IPG 102 to allow the desired parameters to be determined based on patient feedback or other feedback and for subsequently programming the IPG 102 with the desired modulation parameters. To allow the user to perform these functions, the CP 104 may include user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads, and select and program the IPG with modulation parameters, including electrode selection, in both a surgical setting and a clinical setting. The external device(s) (e.g., CP and/or RC) may be configured to communicate with other device(s), including local device(s) and/or remote device(s). For example, wired and/or wireless communication may be used to communicate between or among the devices.

An external charger 112 may be a portable device used to transcutaneous charge the IPG 102 via a wireless link such as an inductive link 113. Once the IPG 102 has been programmed, and its power source has been charged by the external charger or otherwise replenished, the IPG 102 may function as programmed without the RC 103 or CP 104 being present.

Figure 2:
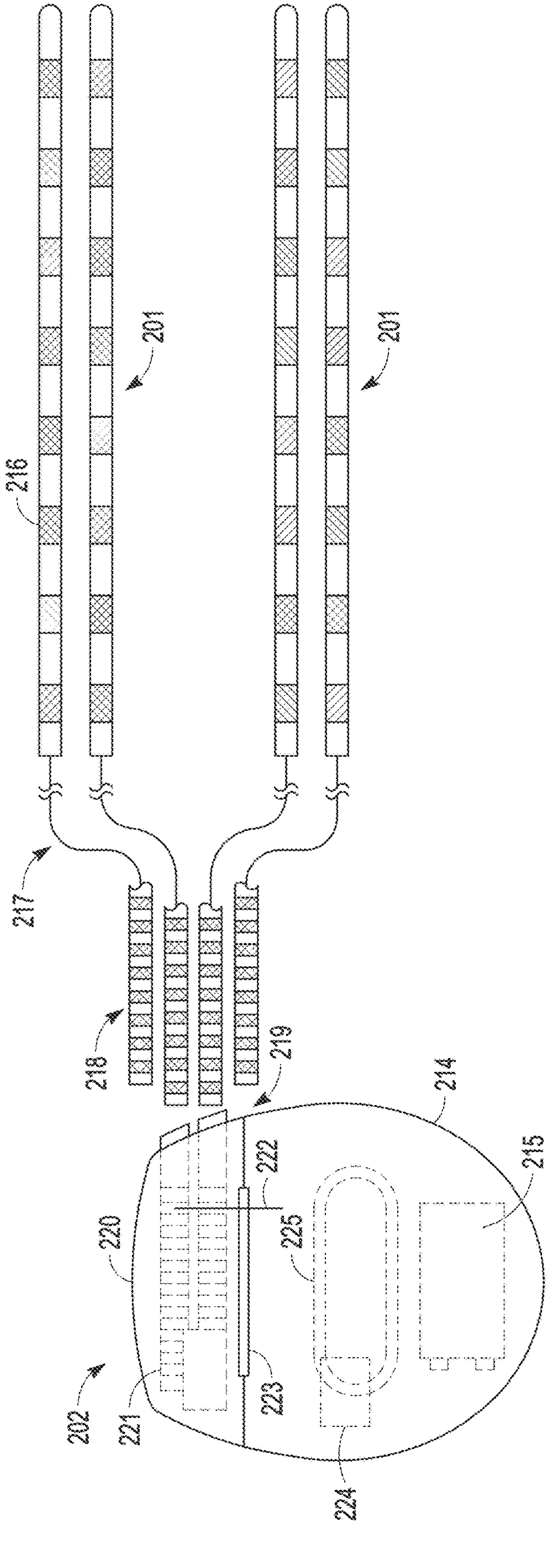
FIG. 2 illustrates, by way of example and not limitation, an implantable pulse generator (IPG) in a DBS system.

FIG. 2 illustrates, by way of example and not limitation, an IPG 202 in a DBS system. The IPG 202, which is an example of the IPG 102 of the electrical stimulation system 100 as illustrated in FIG. 1, may include a biocompatible device case 214 that holds the circuitry and a battery 215 for providing power for the IPG 202 to function, although the IPG 202 can also lack a battery and can be wirelessly powered by an external source. The IPG 202 may be coupled to one or more leads, such as leads 201 as illustrated herein. The leads 201 can each include a plurality of electrodes 216 for delivering electrostimulation energy, recording electrical signals, or both. In some examples, the leads 201 can be rotatable so that the electrodes 216 can be aligned with the target neurons after the neurons have been located such as based on the recorded signals. The electrodes 216 can include one or more ring electrodes, and/or one or more sets of segmented electrodes (or any other combination of electrodes), examples of which are discussed below with reference to FIGS. 3A and 3B.

The leads 201 can be implanted near or within the desired portion of the body to be stimulated. In an example of operations for DBS, access to the desired position in the brain can be accomplished by drilling a hole in the patient's skull or cranium with a cranial drill (commonly referred to as a burr), and coagulating and incising the dura mater, or brain covering. A lead can then be inserted into the cranium and brain tissue with the assistance of a stylet (not shown). The lead can be guided to the target location within the brain using, for example, a stereotactic frame and a microdrive motor system. In some examples, the microdrive motor system can be fully or partially automatic. The microdrive motor system may be configured to perform actions such as inserting, advancing, rotating, or retracing the lead.

Lead wires 217 within the leads may be coupled to the electrodes 216 and to proximal contacts 218 insertable into lead connectors 219 fixed in a header 220 on the IPG 202, which header can comprise an epoxy for example. Alternatively, the proximal contacts 218 may connect to lead extensions (not shown) which are in turn inserted into the lead connectors 219. Once inserted, the proximal contacts 218 connect to header contacts 221 within the lead connectors 219, which are in turn coupled by feedthrough pins 222 through a case feedthrough 223 to stimulation circuitry 224 within the case 214. The type and number of leads, and the number of electrodes, in an IPG is application specific and therefore can vary.

The IPG 202 can include an antenna 225 allowing it to communicate bi-directionally with a number of external devices. The antenna 225 may be a conductive coil within the case 214, although the coil of the antenna 225 may also appear in the header 220. When the antenna 225 is configured as a coil, communication with external devices may occur using near-field magnetic induction. The IPG 225 may also include a Radio-Frequency (RF) antenna. The RF antenna may comprise a patch, slot, or wire, and may operate as a monopole or dipole, and preferably communicates using far-field electromagnetic waves, and may operate in accordance with any number of known RF communication standards, such as Bluetooth, Zigbee, WiFi, MICS, and the like.

In a DBS application, as is useful in the treatment of tremor in Parkinson's disease for example, the IPG 202 is typically implanted under the patient's clavicle (collarbone). The leads 201 (which may be extended by lead extensions, not shown) can be tunneled through and under the neck and the scalp, with the electrodes 216 implanted through holes drilled in the skull and positioned for example in the subthalamic nucleus (STN) and the pedunculopontine nucleus (PPN) in each brain hemisphere. The IPG 202 can also be implanted underneath the scalp closer to the location of the electrodes' implantation. The leads 201, or the extensions, can be integrated with and permanently connected to the IPG 202 in other solutions.

Stimulation in IPG 202 is typically provided by pulses each of which may include one phase or multiple phases. For example, a monopolar stimulation current can be delivered between a lead-based electrode (e.g., one of the electrodes 216) and a case electrode. A bipolar stimulation current can be delivered between two lead-based electrodes (e.g., two of the electrodes 216). Stimulation parameters typically include current amplitude (or voltage amplitude), frequency, pulse width of the pulses or of its individual phases; electrodes selected to provide the stimulation; polarity of such selected electrodes, i.e., whether they act as anodes that source current to the tissue, or cathodes that sink current from the tissue. Each of the electrodes can either be used (an active electrode) or unused (OFF). When the electrode is used, the electrode can be used as an anode or cathode and carry anodic or cathodic current. In some instances, an electrode might be an anode for a period of time and a cathode for a period of time. These and possibly other stimulation parameters taken together comprise a stimulation program that the stimulation circuitry 224 in the IPG 202 can execute to provide therapeutic stimulation to a patient.

In some examples, a measurement device coupled to the muscles or other tissue stimulated by the target neurons, or a unit responsive to the patient or clinician, can be coupled to the IPG 202 or microdrive motor system. The measurement device, user, or clinician can indicate a response by the target muscles or other tissue to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

Figure 3B:
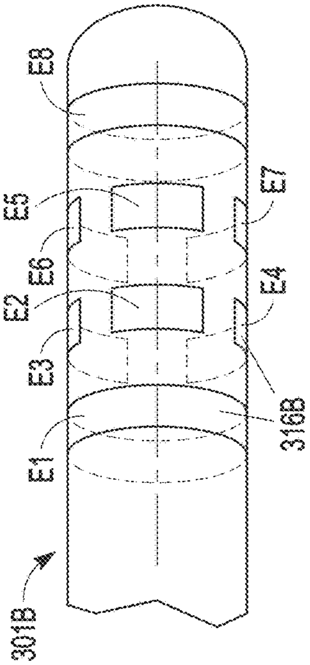
FIGS. 3A-3B illustrate, by way of example and not limitation, leads that may be coupled to the IPG to deliver electrostimulation such as DBS.
Figure 3A:
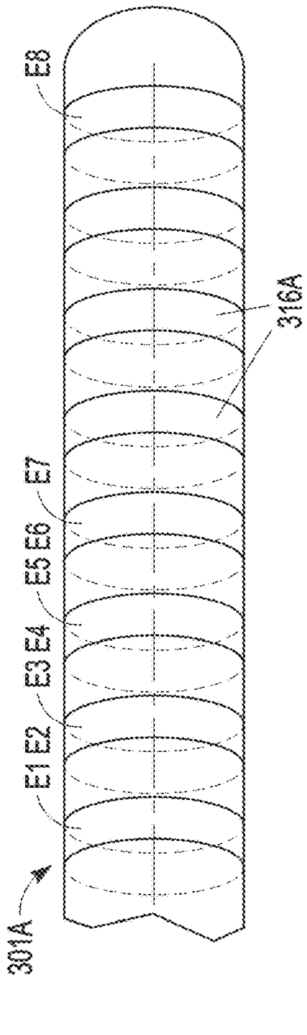

FIGS. 3A-3B illustrate, by way of example and not limitation, leads that may be coupled to the IPG to deliver electrostimulation such as DBS. FIG. 3A shows a lead 301A with electrodes 316A disposed at least partially about a circumference of the lead 301A. The electrodes 316A may be located along a distal end portion of the lead. As illustrated herein, the electrodes 316A are ring electrodes that span 360 degrees about a circumference of the lead 301. A ring electrode allows current to project equally in every direction from the position of the electrode, and typically does not enable stimulus current to be directed from only a particular angular position or a limited angular range around of the lead. A lead which includes only ring electrodes may be referred to as a non-directional lead.

FIG. 3B shows a lead 301B with electrodes 316B including ring electrodes such as E1 at a proximal end and E8 at the distal end. Additionally, the lead 301 also include a plurality of segmented electrodes (also known as split-ring electrodes). For example, a set of segmented electrodes E2, E3, and E4 are around the circumference at a longitudinal position, each spanning less than 360 degrees around the lead axis. In an example, each of electrodes E2, E3, and E4 spans 90 degrees, with each being separated from the others by gaps of 30 degrees. Another set of segmented electrodes E5, E6, and E7 are located around the circumference at another longitudinal position different from the segmented electrodes E2, E3 and E4. Segmented electrodes such as E2-E7 can direct stimulus current to a selected angular range around the lead.

Segmented electrodes can typically provide superior current steering than ring electrodes because target structures in DBS or other stimulation are not typically symmetric about the axis of the distal electrode array. Instead, a target may be located on one side of a plane running through the axis of the lead. Through the use of a radially segmented electrode array, current steering can be performed not only along a length of the lead but also around a circumference of the lead. This provides precise three-dimensional targeting and delivery of the current stimulus to neural target tissue, while potentially avoiding stimulation of other tissue. In some examples, segmented electrodes can be together with ring electrodes. A lead which includes at least one or more segmented electrodes may be referred to as a directional lead. In an example, all electrodes on a directional lead can be segmented electrodes. In another example, there can be different numbers of segmented electrodes at different longitudinal positions.

Segmented electrodes may be grouped into sets of segmented electrodes, where each set is disposed around a circumference at a particular longitudinal location of the directional lead. The directional lead may have any number of segmented electrodes in a given set of segmented electrodes. By way of example and not limitation, a given set may include any number between two to sixteen segmented electrodes. In an example, all sets of segmented electrodes may contain the same number of segmented electrodes. In another example, one set of the segmented electrodes may include a different number of electrodes than at least one other set of segmented electrodes.

The segmented electrodes may vary in size and shape. In some examples, the segmented electrodes are all of the same size, shape, diameter, width or area or any combination thereof. In some examples, the segmented electrodes of each circumferential set (or even all segmented electrodes disposed on the lead) may be identical in size and shape. The sets of segmented electrodes may be positioned in irregular or regular intervals along a length the lead 219.

Figure 4:
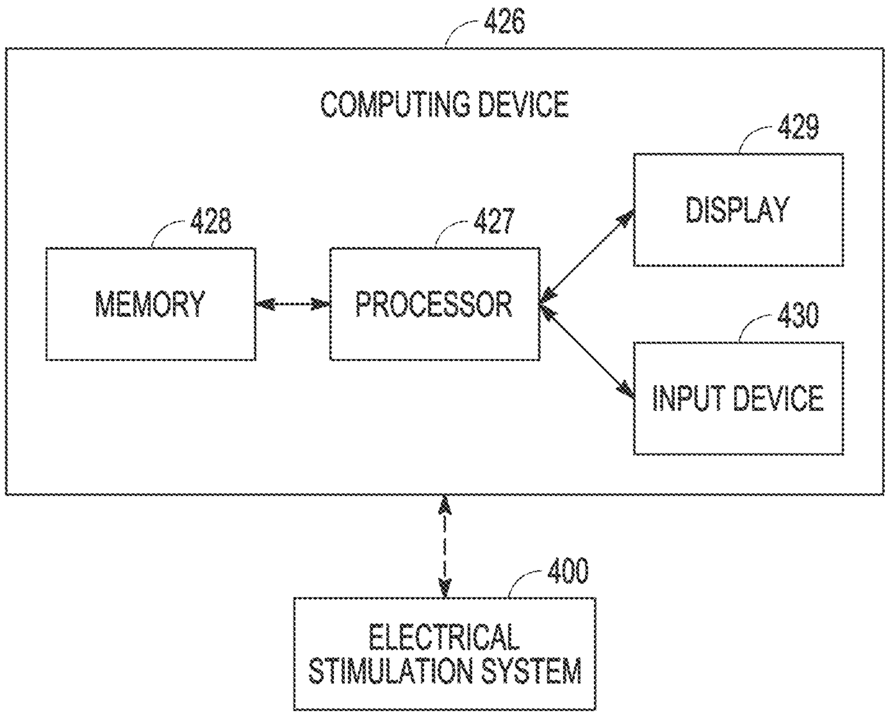
FIG. 4 illustrates, by way of example and not limitation, a computing device for programming or controlling the operation of an electrical stimulation system.

FIG. 4 illustrates, by way of example and not limitation, a computing device 426 for programming or controlling the operation of an electrical stimulation system 400. The computing device 426 may include a processor 427, a memory 428, a display 429, and an input device 430. Optionally, the computing device 426 may be separate from and communicatively coupled to the electrical stimulation system 400, such as system 100 in FIG. 1 Alternatively, the computing device 426 may be integrated with the electrical stimulation system 100, such as part of the IPG 102, RC 103, CP 104, or ETM 105 illustrated in FIG. 1.

The computing device 426, also referred to as a programming device, can be a computer, tablet, mobile device, or any other suitable device for processing information. The computing device 426 can be local to the user or can include components that are non-local to the computer including one or both of the processor 427 or memory 428 (or portions thereof). For example, the user may operate a terminal that is connected to a non-local processor or memory. In some examples, the computing device 406 can include a watch, wristband, smartphone, or the like. Such computing devices can wirelessly communicate with the other components of the electrical stimulation system, such as the CP 104, RC 103, ETM 105, or IPG 102 illustrated in FIG. 1. The computing device 426 may be used for gathering patient information, such as general activity level or present queries or tests to the patient to identify or score pain, depression, stimulation effects or side effects, cognitive ability, or the like. In some examples, the computing device 426 may prompt the patient to take a periodic test (for example, every day) for cognitive ability to monitor, for example, Alzheimer's disease. In some examples, the computing device 426 may detect, or otherwise receive as input, patient clinical responses to electrostimulation such as DBS, and determine or update stimulation parameters using a closed-loop algorithm based on the patient clinical responses, as described below with reference to FIG. 5. Examples of the patient clinical responses may include physiological signals (e.g., heart rate) or motor parameters (e.g., tremor, rigidity, bradykinesia). The computing device 426 may communicate with the axis. CP 104, RC 103, ETM 105, or IPG 102 and direct the changes to the stimulation parameters to one or more of those devices. In some examples, the computing device 426 can be a wearable device used by the patient only during programming sessions. Alternatively, the computing device 426 can be worn all the time and continually or periodically adjust the stimulation parameters. In an example, the closed-loop algorithm for determining or updating stimulation parameters can be implemented in a mobile device, such as a smartphone, that is connected to the IPG or an evaluating device (e.g., a wristband or watch). These devices can also record and send information to the clinician.

The processor 427 may include one or more processors that may be local to the user or non-local to the user or other components of the computing device 426. In an example, the processor 427 may execute instructions (e.g., stored in the memory 428) to determine a search space of electrode configurations and parameter values, and identify or update one or more stimulation settings that are selectable for use in electrostimulation therapies such as DBS. The search space may include a collection of available electrodes, possible electrode configurations, and possible values or value ranges of one or more stimulation parameters that may be applied to selected electrodes to deliver electrostimulation. The search space can be specific to a particular lead or a type of lead with respect to a specific neural target. As a result, for different leads or types of lead and/or for different neural targets, the processor 427 may determine respective different search spaces. A stimulation setting includes an electrode configuration and values for one or more stimulation parameters. The electrode configuration may include information about electrodes (ring electrodes and/or segmented electrodes) selected to be active for delivering stimulation (ON) or inactive (OFF), polarity of the selected electrodes, electrode locations (e.g., longitudinal positions of ring electrodes along the length of a non-directional lead, or longitudinal positions and angular positions of segmented electrodes on a circumference at a longitudinal position of a directional lead), stimulation modes such as monopolar pacing or bipolar pacing, etc. The stimulation parameters may include, for example, current amplitude values, current fractionalization across electrodes, stimulation frequency, stimulation pulse width, etc.

The processor 427 may identify or modify a stimulation setting from the search space through an optimization process until a search criterion is satisfied, such as until an optimal, desired, or acceptable patient clinical response is achieved. Electrostimulation programmed with a setting may be delivered to the patient, clinical effects (including therapeutic effects and/or side effects, or motor symptoms such as bradykinesia, tremor, or rigidity) may be detected, and a clinical response may be evaluated based on the detected clinical effects. When actual electrostimulation is administered, the settings may be referred to as tested settings, and the clinical responses may be referred to as tested clinical responses. In contrast, for a setting in which no electrostimulation is delivered to the patient, clinical effects may be predicted using a computational model based at least on the clinical effects detected from the tested settings, and a clinical response may be estimated using the predicted clinical effects. When no electrostimulation is delivered the settings may be referred to as predicted or estimated settings, and the clinical responses may be referred to as predicted or estimated clinical responses.

In various examples, portions of the functions of the processor 427 may be implemented as a part of a microprocessor circuit. The microprocessor circuit can be a dedicated processor such as a digital signal processor, application specific integrated circuit (ASIC), microprocessor, or other type of processor for processing information. Alternatively, the microprocessor circuit can be a processor that can receive and execute a set of instructions of performing the functions, methods, or techniques described herein.

The memory 428 can store instructions executable by the processor 427 to perform various functions including, for example, determining a reduced or restricted electrode configuration and parameter search space (also referred to as a "restricted search space"), creating or modifying one or more stimulation settings within the restricted search space, etc. The memory 428 may store the search space, the stimulation settings including the "tested" stimulation settings and the "predicted" or "estimated" stimulation settings, clinical effects (e.g., therapeutic effects and/or side effects) and clinical responses for the settings.

The memory 428 may be a computer-readable storage media that includes, for example, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information, and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, Bluetooth™, near field communication, and other wireless media.

The display 429 may be any suitable display or presentation device, such as a monitor, screen, display, or the like, and can include a printer. The display 429 may be a part of a user interface configured to display information about stimulation settings (e.g., electrode configurations and stimulation parameter values and value ranges) and user control elements for programming a stimulation setting into an IPG.

The input device 430 may be, for example, a keyboard, mouse, touch screen, track ball, joystick, voice recognition system, or any combination thereof, or the like. Another input device 430 may be a camera from which the clinician can observe the patient. Yet another input device 430 may a microphone where the patient or clinician can provide responses or queries.

The electrical stimulation system 400 may include, for example, any of the components illustrated in FIG. 1. The electrical stimulation system 400 may communicate with the computing device 426 through a wired or wireless connection or, alternatively or additionally, a user can provide information between the electrical stimulation system 400 and the computing device 426 using a computer-readable medium or by some other mechanism.

Figure 5:
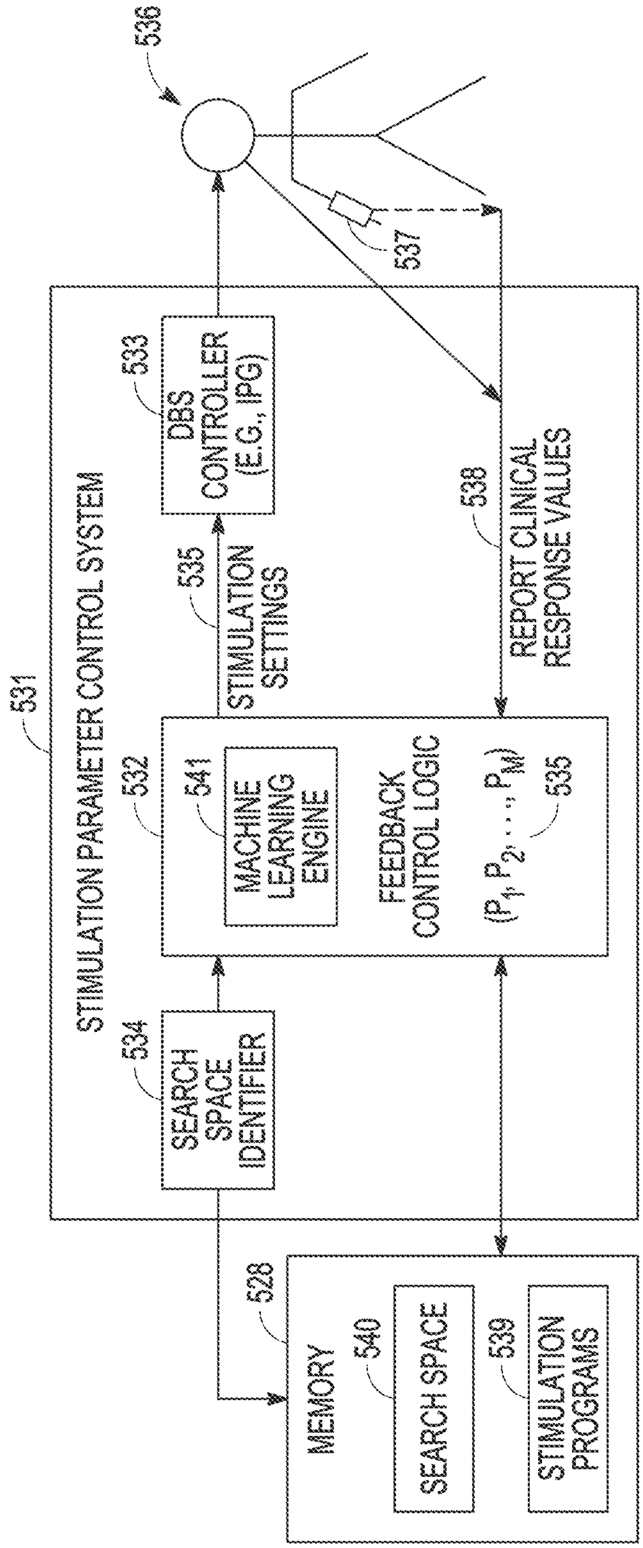
FIG. 5 illustrates, by way of example and not limitation, a stimulation parameter control system and a part of the environment in which it may operate.

FIG. 5 illustrates, by way of example and not limitation, a stimulation parameter control system and a part of the environment in which it may operate. The stimulation parameter control system 531, which may be implemented as a part of the processor 427 in FIG. 4, may include a feedback control logic 532, a DBS controller 533, and a search space identifier 534. The feedback control logic 532 may be implemented in, for example, the CP 104 or the RC 103 in FIG. 1. The feedback control logic 532 can determine or modify one or more stimulation settings 535 for a stimulation lead at a target stimulation region, such as a region in a brain hemisphere. A stimulation setting may include an electrode configuration and values for one or more stimulation parameters ($P_1$, $P_2$, . . . , $P_m$) 536. The electrode configuration includes information about electrodes (ring electrodes and/or segmented electrodes) selected to be active for delivering stimulation (ON) or inactive (OFF), polarity of the selected electrodes, electrode locations (also referred to as contact locations, which may include longitudinal positions of ring electrodes along the length of a lead, or angular positions of segmented electrodes about a circumference of a cross-section of the lead at a longitudinal position), and stimulation modes (e.g., monopolar pacing or bipolar pacing), etc. The stimulation parameters may include, for example, current amplitude values, current fractionalization across electrodes, stimulation frequency, stimulation pulse width, etc. In some examples, the feedback control logic 532 may modify the stimulation setting 535 such as by changing a stimulation parameter value, or modifying an electrode configuration.

The stimulation setting 535 may be provided to the DBS controller 533 to configure the IPG or ETM to deliver DBS therapy to the patient 536 in accordance with the stimulation setting or the modified stimulation setting. The stimulation may produce certain therapeutic effects and/or side effects on the patient 536. Such therapeutic effectiveness and side effects, also referred to as clinical responses or clinical metrics, may be provided to the feedback control logic 532. In an example, the clinical responses may be based on patient or clinician observations. For example, motor symptoms such as bradykinesia (slowness of movement), rigidity, tremor, among other symptoms or side effects, can be scored by the patient or by the clinician upon overserving or questioning the patient. In some examples, the clinical responses can be objective in nature, such as measurements automatically or semi-automatically taken by a sensor 537. In an example, the sensor 537 may be included in a wearable device associated with patient 536, such as a smart watch. For example, a Parkinson's patient may be fitted with a wearable sensor that measures tremors, such as by measuring the frequency and amplitude of such tremors.

The clinical responses, either reported by the patient or measured by a sensor, may be converted to clinical response values 538, also referred to as clinical response scores. In an example, the clinical response values 538 may be computed based on the intensity, frequency, or duration of one or more of tremor, rigidity, or bradykinesia responses. Based upon the received clinical response values 538, the feedback control logic 532 can adjust electrode configurations or values of one or more stimulation parameters 535. The feedback control logic 532 can send the adjusted (new or revised) stimulation setting 535, such as the electrode configuration or the adjusted stimulation parameter values, to further configure the DBS controller 536 to change the stimulation parameters of the leads implanted in patient 506 to the adjusted values.

The feedback-control loop as illustrated in FIG. 5 may continue until an optimal, desired, or acceptable outcome is reached, such as maximizing therapeutic effectiveness while minimizing unwanted side effects, or until a specific stop condition is reached such as number of iterations, time spent in programming session, or the like. An outcome may be considered optimal, desired, or acceptable if it meets certain threshold values or tests (e.g., improved clinical response for the patient, faster programming of the device, increased battery life, and/or control multiple independent current sources and directional lead). Such an iterative process of looking for a stimulation setting (e.g., an electrode configuration and stimulation parameter values for the electrode) is referred to as a stimulation setting optimization process. The outcome being reached is referred to as an optimization criterion, and the resultant stimulation setting is referred to as an optimal base stimulation setting (BSS). By way of example and not limitation, the optimization criterion may include possible optimal clinical outcome within the parameters chosen; time spent, iterations taken, or power usage to explore the search space until a desired clinical outcome is reached (assuming multiple outcomes with the same or comparable clinical response); among others.

In an example, the optimization criterion includes the clinical response values 538 exceeding a threshold value or falling into a specified value range, indicating a satisfactory therapeutic outcome has reached. Depending on how the clinical response values are computed, one or more optimal base stimulation settings may be determined. For example, the clinical response values may be computed using a single response effect (e.g., one of bradykinesia, tremor, or rigidity). Accordingly, three optimal base stimulation settings may be generated: a first optimal base stimulation setting ($BSS_1$) corresponding to a bradykinesia score exceeding a threshold, a second optimal base stimulation setting ($BSS_2$) corresponding to a tremor score exceeding a threshold, and a third optimal base stimulation setting ($BSS_3$) corresponding to a rigidity score exceeding a threshold. In another example, the clinical response values can be a composite score computed as a weighted combination of multiple clinical effects, such as a %*bradykinesia+b %*tremor+c %*rigidity. Accordingly, a fourth optimal base stimulation setting ($BSS_4$) can be generated, corresponding to the composite clinical response score exceeding a threshold. In some examples, the stimulation setting optimization can be performed in an in-clinic programming session such during implantation or revision of a DBS system or device follow-up.

The optimal base stimulation settings (e.g., $BSS_1$ through $BSS_4$), may be stored in the memory 528. In an example, a stimulation setting, along with the corresponding unique clinical response indicator (e.g., weighted combination of clinical effects with unique weight factors) form a stimulation program 539, which can also be stored in the memory 404. Each stimulation programmed can be associated with, or tagged by, one or more unique clinical response indicators. In some examples, the clinical response values 538 may be weighted according to the time at which the test took place, which may correspond to different medication states as discussed in more detail below.

In various examples, the stimulation parameter control system 531 may be executed on its own and is not connected to a controller. In such instances it may be used to merely determine and suggest programming parameters, visualize a parameter space, test potential parameters, etc.

The process of iterative search for a stimulation setting (e.g., an electrode configuration and/or stimulation parameter values) typically involves significant computation and time, especially when electrode configuration involves segmented electrodes in a directional lead. If testing all possible settings in the entire parameter space (including electrode configurations and combinations of stimulation parameter values) is done as comprehensively as possible, stimulation would need to be provided to the patient for each possible setting, which may end up with a burdensome and time-consuming programming session. Because practically a programming session may only last a few hours, only a fraction of possible electrode configuration and stimulation parameter combinations can reasonably be tested and evaluated. To reduce the time taken and to improve the efficiency of stimulation setting optimization process, a reduced or restricted electrode configuration and parameter search space can be used. By applying limitations or constraints to the electrode configurations and parameter values, the restricted search space can include a subset of electrodes (e.g., a subset of ring electrodes and/or a subset of segmented electrodes on a lead) that are selected as active electrodes for delivering stimulation, and values or value ranges for one or more stimulation parameters (e.g., a range of current amplitude ranges for an active electrode). Stimulation setting optimization, when performed within such a search space, can be more efficient and cost-effective than searching through the entire parameter space for one or more optimal base stimulation settings such as $BSS_1$-$BSS_4$ as discussed above.

The search space identifier 534 can automatically determine a search space 540 for a stimulation lead at a neural target, such as a region in a brain hemisphere, by imposing certain limitations or constraints on the electrode configurations and/or parameter values or value ranges. In an example, the search space 540 can be determined based on spatial information of the lead, such as lead positions with respect to neural targets, which can be obtained from imaging data of the lead and patient anatomy. Additionally, or alternatively, the search space 540 can be determined based on physiological information such as physiological signals sensed by the electrodes at their respective tissue contact locations. The physiological information may include patient clinical responses to stimulation. In some examples, prior knowledge about patient medical condition, health status, DBS treatment history may be used to determine the search space 540. In an example, the search space identifier 534 may exclude those electrodes on the lead that are out of a region of interest, such that the search space includes only those electrodes within the target of interest. One or more stimulation parameters may be restricted to take certain values or within value ranges. For example, the restricted search space may include certain electrode positions and value ranges for stimulation current amplitude, frequency, or pulse width. The feedback control logic 532 may determine one or more optimal base stimulation settings (e.g., $BSS_1$-$BSS_4$) by searching through the identified search space 540. The identified search 540 may be stored in the memory 528.

The feedback control logic 532 may include a machine learning engine 541 that can facilitate the stimulation parameter control system 531 (or a user of the system) to explore the search space in order to choose values for programming the DBS controller 533. The machine learning engine 541 can employ supervised or unsupervised learning algorithms to train a prediction model, and use the trained prediction model to predict patient clinical responses to an untested stimulation setting (e.g., untested stimulation parameter values or untested electrode configurations), or to estimate or predict stimulation parameters values or electrode configurations that, when provided to the DBS controller 533 to deliver stimulation accordingly to the patient 536, would produce desired or improved clinical responses. Examples of the learning algorithms include, for example, Naive Bayes classifiers, support vector machines (SVMs), ensemble classifiers, neural networks, Kalman filters, regression analyzers, etc. The machine learning engine 541 can build and train a prediction model using training data, such as stimulation parameter values and corresponding patient clinical responses. The training data can be acquired from a training session such as performed in a clinic. Additionally, or alternatively, the training data can be obtained from historical data acquired by the stimulation parameter control system 531. With its learning and prediction capability, the machine learning engine 541 can aid a user (e.g., a clinician) in exploring the stimulation parameter space more effectively and more efficiently to produce results that are optimal, desired, or acceptable.

In some examples, the machine learning engine 541 can use imaging data to inform the choice of the next set of values, which may be used when the algorithm finds itself in a region of parameter space for which the clinical responses are not substantially affected by the changes in the stimulation parameters, and the choice of next step is not apparent from the patient response alone. Imaging data that provides information about the location of the lead in the patient's brain along with priors informing the algorithm of which directions may be better choices for the next step could lead to faster convergence.

In some examples, the machine learning engine 541 can determine expected outcomes for parameter values that have not yet been tested based upon what the machine learning engine 541 has "learned" thus far, and provide a recommendation for a next set of values to test. Here, testing refers to the iterative testing required to find an optimal stimulation setting for configuring the DBS controller 533. The recommendation for a next set of values to test is based upon which of the determined expected outcomes meet a set of designated (determined, selected, preselected, etc.) criteria (e.g., rules, heuristics, factors, and the like). For example, rules considered may include such factors as: the next set of values cannot be one of the last 10 settings tested or cannot be too close to previously tested setting. Accordingly, the feedback control logic 532 with its machine learning engine 541 is used to systematically explore the stimulation parameter space based upon what it has learned thus far and (optionally) different rules and/or heuristics that contribute to achieving optimal outcomes more efficiently.

The process for determining expected outcomes for parameter values that have not yet been tested may involve use of other data for machine learning. For example, data from other programming sessions for the same patient as well as from other patients may be used to train the machine learning engine 541. In some examples, no prior data may be used. In this case, the machine learning engine 541 may use data learned from this patient only in one particular setting. In other examples, data from the same patient but from previous sessions may be used. In some examples all patient data from all sessions may be used. In some examples all patient data utilizing lead location information (knowledge of lead location in space relative to anatomy) may be used. Different other combinations are also possible.

In order to use this data for machine learning purposes, the data may first be cleansed, optionally transformed, and then modeled. In some examples, new variables are derived, such as for use with directional leads, including central point of stimulation, maximum radius, spread of stimulation field, or the like. Data cleansing and transformation techniques such as missing data imputation and dimension reduction may be employed to prepare the data for modeling.

The machine learning engine 541 may determine how best a predicted outcome meets the optimal outcome metrics. Various optimization techniques may be used, examples of which may include but are not limited to: optimization algorithms and estimation procedures used to fit the model to the data (e.g., gradient descent, Kalman filter, Markov chain, Monte Carlo, and the like); optimization algorithms reformulated for search (e.g., simulated annealing); spatial interpolation (e.g., kriging, inverse distance weighting, natural neighbor, etc.); supplementary methods that aid the optimization process (e.g., variable selections, regularization, cross validation, etc.); other search algorithms (e.g., golden-section search, binary search, etc.). Using any of these techniques, the machine learning engine 541 can decide whether a particular predicted outcome for a set of stimulation parameter values is the fastest sufficing outcome, the best possible clinical outcome, or the optimal outcome with least battery usage, for example.

The feedback control logic 532 may be used to search and configure different types of stimulation parameters of the various leads potentially causing different clinical effects upon the patient 536. Examples of the stimulation parameters may include electrode configurations (electrode selection, polarities, monopolar or bipolar modes of stimulation), current fractionalization, current amplitude, pulse width, frequency, among others. Given these possible stimulation parameters, the stimulation parameter control system 531 can move about the parameter space in different orders, by different increments, and limited to specific ranges. In some examples, the stimulation parameter control system 531 may allow the user to provide search range limitations to one or more of the stimulation parameters to limit the range for that stimulation parameter over which the system will search for parameters. For example, the user may restrict which electrodes can be used for stimulation or may restrict the amplitude or pulse width to a certain range or with a selected maximum or minimum. As one illustration, based on the site of implantation, the user may be aware that the distal-most and proximal-most electrodes are unlikely to produce suitable stimulation and the user limits the range of electrodes to exclude these two electrodes.

For a lead with segmented electrodes, the number of possibilities for parameter selection can be very large when combinations of electrodes and different amplitudes on each electrode are possible. In some examples using a lead with segmented electrodes, the selection of electrodes used for stimulation may be limited to fully directional selections (i.e., selection of only a single segmented electrode) and fully concentric selections (i.e., all electrodes in a single set of segmented electrodes are active with the same amplitude). In other examples, the initial movement through parameter space may be limited to fully directional and fully concentric selections. After a set of stimulation parameters is identified using these limits, variation in the selection of electrodes may be opened up to other possibilities near the selection in the identified set of stimulation parameters to further optimize the stimulation parameters.

In some examples, the number of stimulation parameters that are varied and the range of those variations may be limited. For example, some stimulation parameters (e.g., electrode selection, amplitude, and pulse width) may have larger effects when varied than other stimulation parameters (e.g., pulse shape or pulse duration). The movement through stimulation parameter space may be limited to those stimulation parameters which exhibit larger effects. In some examples, as the stimulation parameter control system 531 proceeds through testing of sets of stimulation parameters, the system may observe which stimulation parameters provide larger effects when varied and focus on exploring variation in those stimulation parameters.

In some examples, the stimulation parameter control system 531 can include a user interface for visualizing exploration of the stimulation parameter space as the system determines new and better parameter values to test until a solution is determined that fits within certain designated thresholds or a stop condition is reached. In some examples of the stimulation parameter control system 531, the user interface is part of the feedback control logic 535. In other examples, the user interface may be part of another computing system that is part of the stimulation parameter control system 531 or may be remote and communicatively connected to the stimulation parameter control system 531. The user interface may present to a user (such as a clinician, physician, programmer, etc.) a visualization of the predicted expected outcomes for (some of) the stimulation parameter values not yet tested and a recommendation for the next set of stimulation parameter values to test.

In some examples where a deep brain stimulator is configured via the DBS controller 533 with at least one set of stimulation parameter values forwarded by the feedback control logic 532, the clinician may monitor the patient throughout the process and record clinical observables in addition to the patient 536 being able to report side effects. When a side effect is observed, the various search algorithms may take that fact into account when selecting/suggesting a next set of values to test. In some examples, for example, those that select contacts via monopolar review, other parameters may be changed until they cause a side effect, which case is noted as a boundary. For example, in monopolar review where amplitude is another stimulation parameter being varied, the amplitude may be increased progressively until a side-effect is observed.

In some examples, more than one clinical metric (e.g., tremor, rigidity, bradykinesia, etc.) may be important observables. Different examples of the stimulation parameter control system 531 may handle these metrics differently. For example, some examples might identify an ideal location for each metric and choose one ideal location between them, set in the patient's remote controller so the patient can choose as needed, or chose a best combined outcome. As another example, some examples may search multiple outcomes at the same time and use the best combined score as the best outcome or find a best location for each metric individually. As yet another example, some examples may use a sequential process for selecting stimulation parameter values for multiple outcomes. For example, a system may search parameter space for a first outcome (e.g., bradykinesia) and, upon finding a suitable end condition, then search parameter space for a second outcome (e.g., rigidity). While searching parameter space for the first outcome, clinical response values for both the first and second outcomes can be obtained. Thus, when the system switches to the second outcome there are already a number of clinical response values for that outcome which will likely reduce the length of the search.

In some examples, two stimulation leads may be implanted to produce stimulation effects on two sides of the body (e.g., the right and left sides of the body). The same procedure described herein can be used to either jointly determine the stimulation parameters for the two leads by exploring the joint parameter space or individually determine stimulation parameters for the two leads by exploring the parameter space for each lead individually. In some examples, the user may determine for each side of the body which clinical response is dominant or most responsive. This may be done, for example, by having the patient perform a single task which captures multiple responses (e.g., connecting dots on the screen to monitor tremor and bradykinesia of the movement) or a small series of tasks. This enables the system to determine which clinical response to use to identify the stimulation parameters for that side of the body.

As noted, the feedback may be provided directly by the patient 536, entered by an observer such as a clinician (not shown), or may be provided by means of a sensor 537 associated with and in physical, auditory, or visual contact with the patient 536. In an example, the sensor 537 may be included in a wearable device associated with patient 536, such as a smart watch. In an example where the feedback can be monitored automatically or semi-automatically, such as with use of sensor 537, it may not be necessary for a clinician or other observer to be present to operate the stimulation parameter control system 531. Accordingly, in such examples a user interface may not be present in system 531.

In some examples, the stimulation parameter control system 531 may determine one or more optimal base stimulation settings using predicted clinical responses for untested stimulation parameter values or untested electrode configurations without actually delivering stimulation. Such base stimulation settings are referred to as estimated or predicted base stimulation settings, to distinguish from the tested base stimulation settings (e.g., $BSS_1$-$BSS_4$) that are based on the tested clinical response (either reported by the patient or measured by a sensor) to actually delivered stimulation. For examples, based on the "tested" base stimulation settings $BSS_1$-$BSS_4$, the stimulation parameter control system 531 may estimate an optimal base stimulation setting associated with a composite clinical response defined as x %*bradykinesia+y %*tremor+z %*rigidity, or simply denoted by the weight factors (x %, y %, z %). By way of example and not limitation, the stimulation parameter control system 531 may generate a fifth optimal base stimulation setting ($BSS_5$) corresponding to a composite clinical response using bradykinesia and tremor only, each weighted 50%; a sixth optimal base stimulation setting ($BSS_6$) corresponding to a composite clinical response using tremor and rigidity only, each weighted 50%; a seventh optimal base stimulation setting ($BSS_7$) corresponding to a composite clinical response using bradykinesia and rigidity only, each weighted 50%; or an eighth optimal base stimulation setting ($BSS_8$) corresponding to a composite clinical response using bradykinesia, tremor, and rigidity weighted 40%, 40%, and 20%, respectively. Similar to the tested base stimulation settings $BSS_1$-$BSS_4$, the estimated base stimulation settings $BSS_5$-$BSS_8$, associated with their respective clinical response indicators (e.g., weight factors for clinical effects), can be stored in the memory 528 as respective stimulation programs 539. In an example, the stimulation programs 539 may be stored in a lookup table, where each tested or estimated base stimulation setting (e.g., $BSS_1$ through $BSS_8$) may be tagged by respective clinical response indicators or weight factors for clinical effects. In an example, the memory 528 can be a part of memory circuitry internal to the IPG. The RC or the CP can request access to the memory 528 to retrieve therefrom one or more stored stimulation programs 539 or the search space 540.

Figure 6:
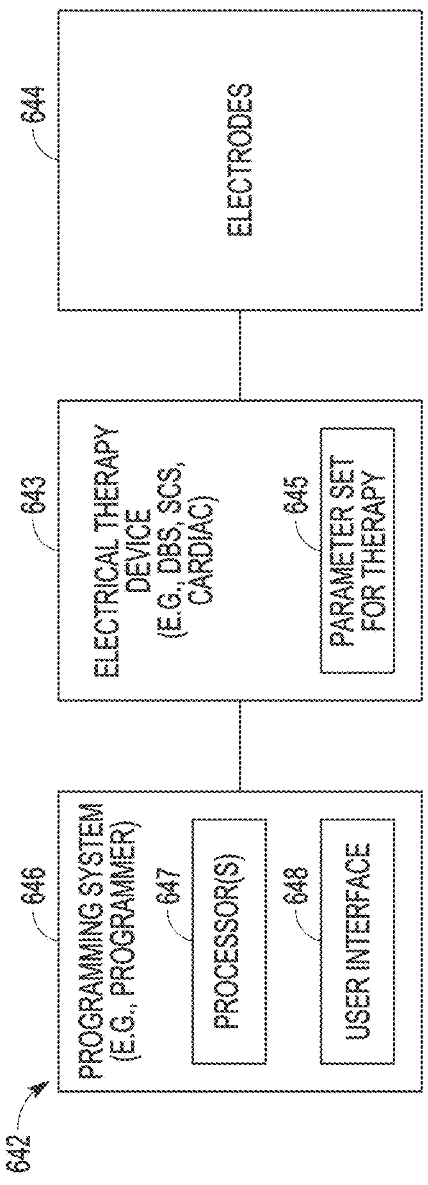
FIG. 6 illustrates, by way of example, an example of an electrical therapy-delivery system.

FIG. 6 illustrates, by way of example, an example of an electrical therapy-delivery system. The illustrated system 642 includes an electrical therapy device 643 configured to deliver an electrical therapy to electrodes 644 to treat a condition in accordance with a programmed parameter set 645 for the therapy. The system 642 may include a processing system 646 that may include one or more processors 647 and a user interface 648, which may be used to program and/or evaluate the parameter set(s) used to deliver the therapy. The illustrated system 642 may be a DBS system for treating a movement disorder, such as has been illustrated and discussed with respect to FIGS. 1-5, and/or a system for monitoring the movement disorder.

In some embodiments, the illustrated system 642 may include an SCS system to treat pain and/or a system for monitoring pain. By way of example, a therapeutic goal for conventional SCS programming may be to maximize stimulation (i.e., recruitment) of the dorsal column (DC) fibers that run in the white matter along the longitudinal axis of the spinal cord and minimal stimulation of other fibers that run perpendicular to the longitudinal axis of the spinal cord (e.g., dorsal root fibers). While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been conventionally targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. SCS systems may deliver sub-perception therapy that is therapeutically effective to treat pain, for example, but the patient does not sense the delivery of the modulation field (e.g., paresthesia). SCS systems may selectively modulate some tissue over other tissue (e.g., selectively stimulate DR tissue and/or dorsal root ganglion over DC tissue) to provide sub-perception therapy. By way of example and not limitation, SCS modulation may be delivered with different waveforms which may but does not necessarily include a train of pulses. The pulses may be delivered using one more amplitudes, pulse widths, pulse-to-pulse intervals, pulse frequency(ies), a duty cycle, in which stimulation (e.g., a burst or train of pulses) is delivered during a Stimulation ON portion of the duty cycle, and is not delivered during a Stimulation OFF portion of the duty cycle, and one or more burst-to-burst intervals. Neuromodulation, such as SCS, is not limited to pulses, but may include other electrical waveforms (e.g., waveforms with different waveform shapes, and waveforms with various pulse patterns) delivered using one or more leads and a plurality of electrodes distributed in an electrode arrangement using the one or more leads. The number of leads and the number of electrodes on each lead may depend on, for example, the distribution of target(s) of the neuromodulation and the need for controlling the distribution of electric field at each target. The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical waveforms (e.g., pulses), presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

In some embodiments, the illustrated system 642 may include a cardiac therapy system to treat cardiovascular conditions and/or a system to monitor the cardiovascular conditions. Examples may include an implantable cardiac monitor (ICM), a pacemaker, a defibrillator, a cardiac resynchronizer, or other subcutaneous implantable medical device or cardiac rhythm management (CRM) device configured to be implanted in a chest of a subject, having one or more leads to position one or more electrodes or other sensors at various locations in or near the heart, such as in one or more of the atria or ventricles. Separate from, or in addition to, the one or more electrodes or other sensors of the leads, the implantable medical device may include one or more electrodes or other sensors (e.g., a pressure sensor, an accelerometer, a gyroscope, a microphone, etc.) powered by a power source in the implantable medical device, which may be configured detect physiologic information from, or provide one or more therapies or stimulation to, the patient.

Implantable devices can additionally include a leadless cardiac pacemaker (LCP), small (e.g., smaller than traditional implantable devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable device complications (e.g., required incision and pocket, complications associated with lead placement, breakage, or migration, etc.). In certain examples, a leadless cardiac pacemaker can have more limited power and processing capabilities than a traditional CRM device; however, multiple leadless cardiac pacemaker devices can be implanted in or about the heart to detect physiologic information from, or provide one or more therapies or stimulation to, one or more chambers of the heart. The multiple LCP devices can communicate between themselves, or one or more other implanted or external devices.

The present subject matter may be implemented with other therapies. By way of example and not limitation, the present subject matter may be implemented for bladder stimulation or bowel stimulation.

Figure 7:
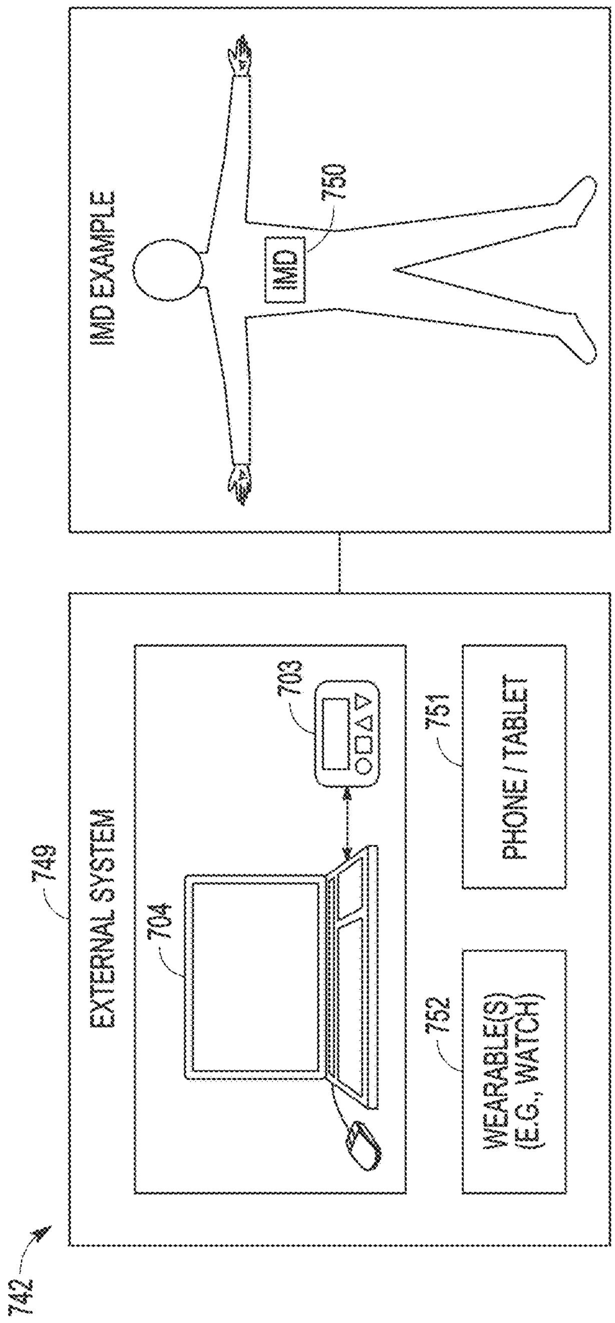
FIG. 7 illustrates, by way of example and not limitation, a monitoring system and/or the electrical therapy-delivery system of FIG. 6, implemented using an implantable medical device (IMD).

FIG. 7 illustrates, by way of example and not limitation, a monitoring system and/or the electrical therapy-delivery system of FIG. 6, implemented using an implantable medical device (IMD). The illustrated system 742 includes an external system 749 that may include at least one programming device. The illustrated external system 749 may include a clinician programmer 704, similar to CP 104 in FIG. 1, configured for use by a clinician to communicate with and program the neuromodulator, and a remote control device 703, similar to RC 103 in FIG. 1, configured for use by the patient to communicate with and program the neuromodulator. For example, the remote control device 703 may allow the patient to turn a therapy on and off and/or may allow the patient to adjust patient-programmable parameter (s) of the plurality of modulation parameters. FIG. 7 illustrates an IMD 750, although the monitor and/or therapy device may be an external device such as a wearable device. The external system 749 may include a network of computers, including computer(s) remotely located from the IMD 750 that are capable of communicating via one or more communication networks with the programmer 704 and/or the remote control device 703. The remotely located computer(s) and the IMD 750 may be configured to communicate with each other via another external device such as the programmer 704 or the remote control device 703. The remote control device 703 and/or the programmer 704 may allow a user (e.g., patient and/or clinician or rep) to answer questions as part of a data collection process. The external system 749 may include personal devices such as a phone or tablet 751, wearables such as a watch 752, sensors or therapy-applying devices. The watch may include sensor(s), such as sensor(s) for detecting activity, motion and/or posture. Other wearable sensor(s) may be configured for use to detect activity, motion and/or posture of the patient. The external system 749 may include, but is not limited to, a phone and/or a tablet.

Figure 8:
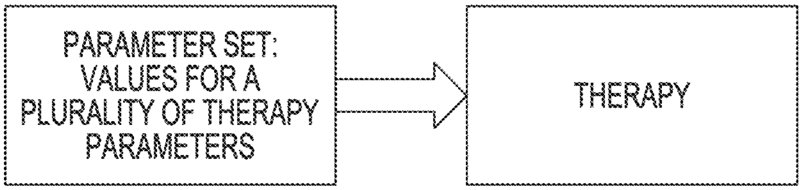
FIG. 8 illustrates a therapy being delivered according to a parameter set.

FIG. 8 illustrates a therapy being delivered according to a parameter set. The parameter set may be programmed into the device to deliver the specific therapy using specific values for a plurality of therapy parameters. For example, the therapy parameters that control the therapy may include pulse amplitude, pulse frequency, pulse width, and electrode configuration (e.g., selected electrodes, polarity and fractionalization). The parameter set includes specific values for the therapy parameters.

Figure 9:
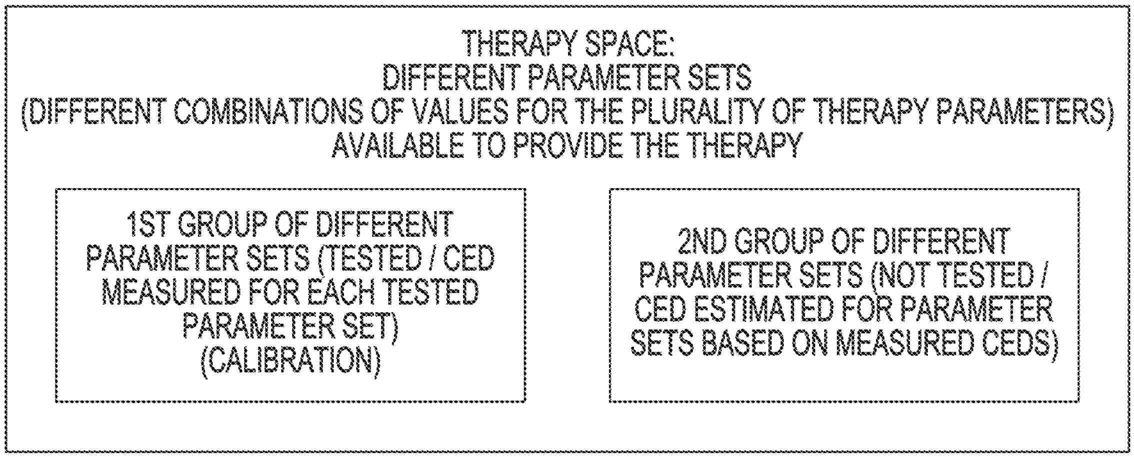
FIG. 9 illustrates a therapy space, which includes different parameter sets potentially available to configure the therapy.

FIG. 9 illustrates a therapy space, which includes different parameter sets potentially available for delivering the therapy. The different parameter sets have unique combinations of values for the therapy parameters. It is again noted that the therapy space can be burdensomely large as there may be many unique combinations of values for therapy parameters (e.g., many unique parameter sets). Some parameter sets within the therapy space may be tested and the corresponding CED may be measured or otherwise acquired for the tested parameter sets. These tested parameter sets are illustrated as a first group of different parameter sets within the therapy space. Other parameter sets may not be tested (e.g., second group of different parameter sets). The CED for these parameter sets may be estimated based on measured CEDs for the patient or a patient population.

For example, CED may be directly measured to provide calibration settings. The therapy sessions may be delivered using different therapy settings, and the CED may be recorded for each session. For a neurostimulator such as DBS, SCS, PNS or TENS, for example, the therapy may involve delivering electrical waveforms, which may be a pulsed waveform. Programmable settings for the pulse waveform may include a pulse amplitude, a pulse width, a pulse frequency, a pulse train duration, a pulse-to-pulse duty cycle, a pulse train to pulse train duty cycle (stimulation ON/OFF), and a stimulation schedule (e.g., programmable start and/or stop times, such as but not necessarily a calendar-based schedule). The programmable settings may further include controlling which of a plurality of electrodes are active and which are off, the polarity of each active electrode (which active electrode(s) are anode(s) and which are cathode(s), and the contributes (e.g., electrode fractionalization) of total energy delivered to individual one(s) of the anode(s) and individual one(s) of the cathode(s). Thus, by way of example and not limitation, one electrode may be programmed to provide all (100%) of the anodic energy, and four electrodes may be programmed to provide fractions (e.g., 25%, 25%, 25%, 25%; or 10%, 20%, 30% and 40%) of the total cathodic energy. Controlling the individual contributions by individual electrodes adjusts the location and shape of the stimulation field, to modulate different combinations of neural elements. The settings may be spread throughout the stimulation space for use in identifying clinical responses from session to session, including both the previously-measured clinical effects for tested stimulation settings and predicted or estimated clinical effects for stimulation settings that were not previously tested.

Patients whose CED are being monitored may be treated with medication. For example, the conditions being treated using a therapy-delivery device may also be treating the same conditions with medication. By way of non-limiting examples, a patient with PD may use a medicine such as levodopa to treat bradykinesia; a patient with pain may use opioids, anti-inflammatory drugs such as non-steroidal anti-inflammatory drugs (NSAIDS) or analgesics, non-opioid pain medicine, and combinations thereof; and a cardiovascular patient may take beta blockers, ACE inhibitors, vasodilators, diuretics, anticoagulants, and the like. Even if the same conditions are not being treated, the medications may still affect the acquired CED.

The present inventors recognize that the acquired CED may be dependent on a medication state of the patient. For example, the therapy-delivery devices may be treating a condition that is also affected by medicine. Therefore, the clinical effects used to monitor the efficacy of the device therapy and program settings may be affected by medications that are taken by the patient. For example, when DBS patients are treated with both medication and stimulation to manage their motor symptoms, the patient's motor symptoms can thus fluctuate depending on where they are in their medication cycle.

Figure 10:
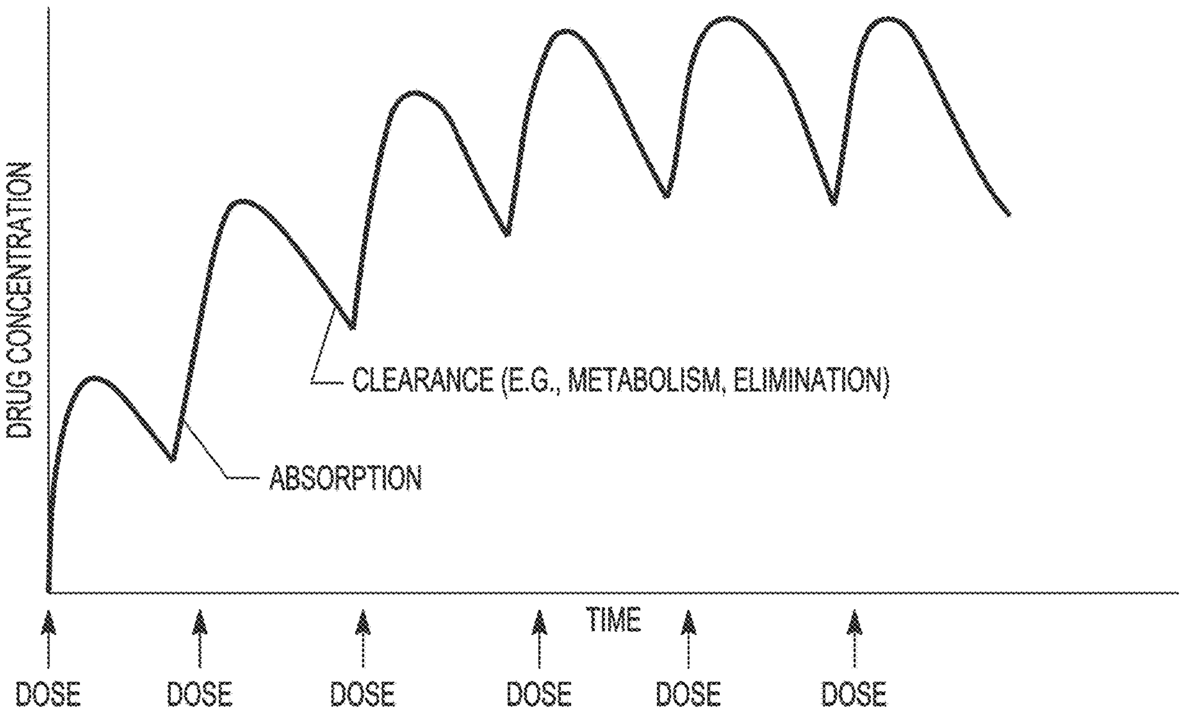
FIG. 10 illustrates, by way of example, drug concentration fluctuations over the course of multiple doses of the medicine.

FIG. 10 illustrates, by way of example, drug concentration fluctuations over the course of multiple doses of the medicine. For example, drug concentration may take multiple doses (illustrated as about 5 doses) before the drug concentrations reach a stead state of fluctuations. Up until that time, the drug concentrations are generally increasing over several doses until the steady state is reached. However, through the course of administering the medication, the drug concentration varies, as it generally increases as a dose is absorbed and then decreases with drug clearance through metabolism and elimination. These fluctuations can make diaries of motor symptoms, whether they are collected in clinic or through remote monitoring means, difficult to correlate between sessions.

Various embodiments of the present subject matter account for medication state to improve clinical effect data (CED) capture and programming by measuring and/or predicting the impact of various medications states on CED. The CED may be translated for various medication states, so that CED for one medication state may be compared to CED for another medication state. It is noted that, as generally illustrated by the drug fluctuations in FIG. 10, the medicated state may be more than just a medicated/unmedicated states, as a concentration of a single medication fluctuates based on the dose, the dose interval, the absorption rate, and the clearance rate (e.g., metabolism, elimination). Further, it can take several doses of a medicine to reach a steady state. Even at a steady state, the concentration of medicine still fluctuates between doses. Drug metabolism rate varies for different drugs, and the metabolism rate for the same drug may vary among patients. Factors that may affect drug metabolism rate include genetics, coexisting disorders, diet, and drug interactions. Many patients may be taking multiple drugs, with different drugs being taken at different times and different doses. The present subject matter may account for all medicines that can affect the CED. The medication state may be acquired for each drug individually, or may be acquired for the drugs in combination. Various embodiments are capable of predicting and/or incorporating the patient's medication state, and adjusting the recorded CED data accordingly or otherwise take medication state into account allowing an algorithm or clinical programmer to suggest/implement an updated stimulation setting.

The medication state may be determined using sensor(s), timer(s), patient or other user input, and various combinations thereof. By way of example and not limitation, examples of sensor(s) that may infer a medication state may include neural sensors configured for use in detecting a characteristic change in sensed neural activity. The neural sensors may be used in detecting change(s) in evoked neural activity. Other sensor examples include chemical sensors for detecting molecules withing the body (e.g., dopamine sensors). Examples of sensor(s) may include external and/or internal sensor(s) configured for use in detecting a characteristic shift in the treated condition (e.g., accelerometer(s) capable of detecting movements for use in detecting a characteristic shift in movement disorders such as tremor/bradykinesia/dyskinesia), or blood pressure, pulse rate or electrocardiogram (ECG) sensors that may be used to monitor cardiovascular health, or sensor(s) that may be used to infer changes in pain (e.g., galvanic skin response, heart rate, blood pressure, posture, motions and/or facial recognition sensor(s)). Sensor(s) may be configured to detect the concentration of the medicine within the patient.

The system may associate programmable timer(s) with the patient's medication schedule to determine a medication state. A system may essentially assume that the patient is taking medication as directed, and is expected to have typical concentration variations in view of the scheduled dosing for the medication. The typical concentration variations may be determined based on evaluations of variations in the patient and/or based on evaluations of patient populations. The timers may be incorporated into a clinical programmer, a remote control, a patient's personal device (e.g., smart phone or tablet), or the medical device (e.g., implantable device).

The medication state may be determined using patient input, which may include a notification by the patient through interaction with the medical device, the remote control, the patient's personal device, and the like to indicate that medication was taken. The patient input may indicate the dose and time that the medication was taken. The input may be provided by another user such as a clinician, a family member, or other healthcare givers. Mood assessments and cognitive scores may provide CED for some disorders, and may also infer medication state.

Figure 11:
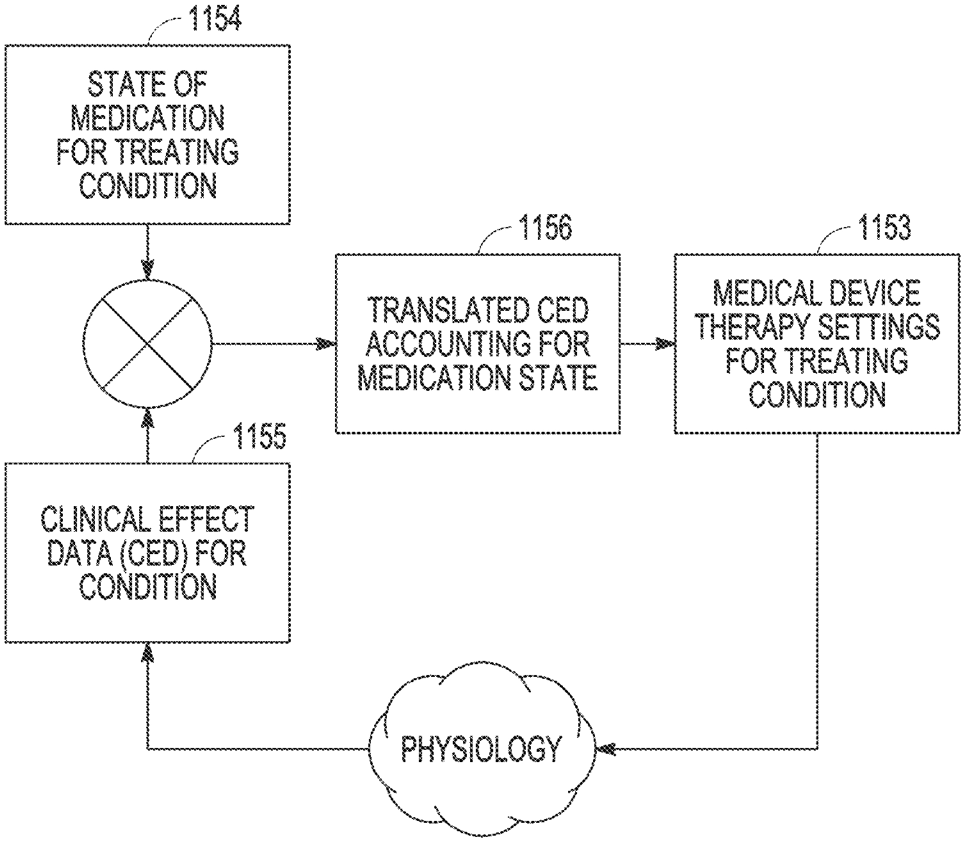
FIG. 11 illustrates, by way of example and not limitation, an example for adjusting medical device therapy settings using CED and medications state.

FIG. 11 illustrates, by way of example and not limitation, an example for adjusting medical device therapy settings using CED and medications state. A medical device may be delivering a therapy to treat a condition using medical device therapy settings 1153. The delivered therapy is intended to have a desired effect and/or is desired to avoid negative effects on the patient's physiology. In the illustrated example, the estimated or determined state of medication may be acquired at 1154 (e.g., patient input, patient schedule and/or sensors that allow the medication state to be determined or inferred), and the CED may be acquired at 1155 (e.g., sensors and/or patient input that allow the CED to be determined or inferred). The CED may be detected in real-time, or may have been previously detected and stored without associate with a medication state, and then later associated with the medication state. The CED and the medication state are used to translate the CED for the medication state 1156, and the translated CED may be used to update the medical device therapy settings 1153.

The search space may be recalibrated to account for fluctuations in clinical responses. For example, error bars may be set for the CED. It is noted that clinical effects may vary over repeated measurements under identical situations. For example, sensors have some variability. However, these slight variations in the clinical effect do not represent a meaningful change in clinical benefit, but rather represent error within the system. As such each recorded setting will be fixed with an error bar proportional to its anticipated error rate. If using a wearable this could be provided based on clinical studies conducted by the manufacturer. This can further be derived from literature or clinical studies, or clinical benefits may be assessed manually (e.g., user input) or via a wearable sensor(s).

The CED for previously untested settings may be predicted. These predictions for the untested settings may be recalibrated based on prior data obtained from the patient or from other patients. An algorithm may be used predict a CED change resulting from the current medication state, or otherwise weight the prior data. By way of example and not limitation, bradykinesia has been shown to improve with levodopa but tremor may be less responsive, which can be true for the patient or generalized from the population. Thus, the patient's overall bradykinesia response maybe predicted to improve by "1" across all CED points when in a maximal medication state. However, because tremor is not as responsive to the medication, tremor may be only predicted to improve by 0.5 across the space when in a maximal medication state.

The predicted CED may be verified. Predicated values may be weighted to determined which should be tested to confirm predictions. For example, predicted values weighted based on greatest significance and distance from calibration values may be tested to confirm predictions. If the predicted scores fall within the set error bars, then those predictions can be confirmed and no adjustments are needed. If the predicted scores fall outside of the set error bars but a transition of the calibration settings within their error bars brings the predicted score into an error bar range, the map may be adapted to best fit all points. If the predicted scores fall outside of the set error bars and no transition of the calibration settings within their error bars brings the predicted score into an error bar range, then the new value may be input and used to update the prediction map. Additionally, a region of lower confidence may surround the predicted values closest to the poorly predicted point, and this lower confidence area may be increasingly explored by an optimizer.

Alternatively, the medication state may be a dimension in the CED vector or matrix and used by the optimizer directly (rather than indirectly including the medication state information through a predicted clinical effect). The settings evaluated at each session (e.g., the "calibration settings") can be used to provide sufficient data context for the optimizer to use the information effectively. Another means of providing sufficient data context is to use data from prior experiences with one or more other patients.

Thus, the clinical effects map is dynamic, as it can be updated as new parameter sets are tested. However, it is important to be able to estimate clinical effects for many parameter sets as it may take significant amount of time for symptoms to wash-out and wash-in with parameter set changes. For example, side effects (e.g., mood) may take days to wash-in, whereas other effects (tremor/rigidity) may respond to parameter set changes within minutes.

Figure 12:
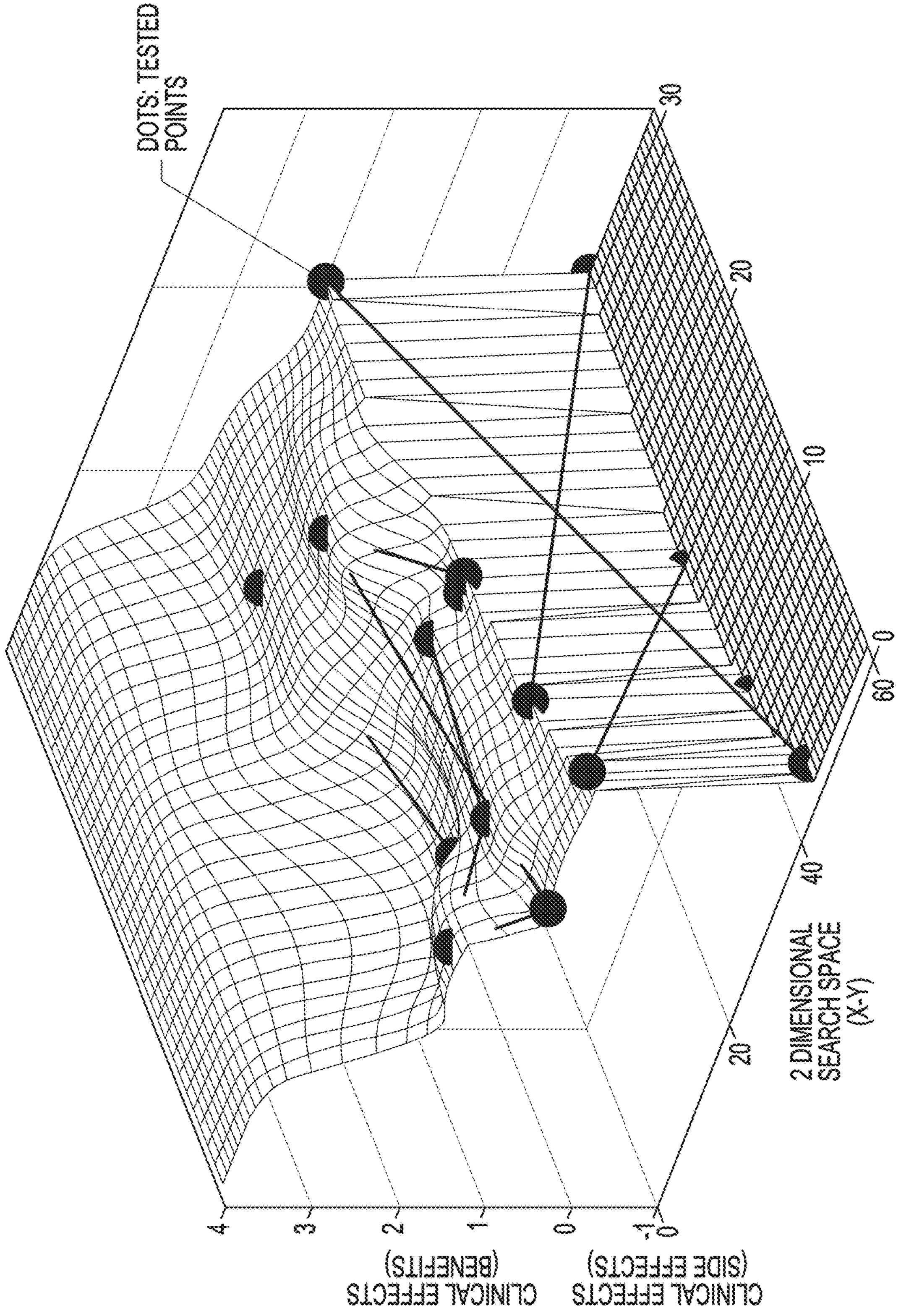
FIG. 12 illustrates, by way of example and not limitation, a heatmap of stimulation outcomes.

FIG. 12 illustrates, by way of example and not limitation, a heatmap of stimulation outcomes. The heat map includes tested points ("dots") and estimated points (other points in heat map). For ease in visualizing a three-dimensional heatmap, the search space has two parameters to provide an X-Y plane. More particularly, by way of example, the X-Y plane in the illustration represents pulse amplitude (0-60 axis) and electrode (0-30). The Z-axis (height) represents clinical effects, where positive values are benefits and negative values are side effects. It is noted that the search space may include many more parameters than two parameters. In updating predictions, the entire plane of the map may be shifted based on patient state as determined by the calibration settings. However chronic changes or known treatment fluctuations may disproportionately effect difference regions of the search space.

The present subject matter may be used in clinic. For example, CED translation may be used to adjust pre-collected CED to a current patient state. A benefit is to adjust preexisting CED to align with the patient's current state, allowing the user to utilize preexisting data with confidence in order to update a patient's treatment without increasing the testing burden.

In another example, CED translation may be used to understand patient change, regardless of whether the change is caused by an acute or chronic condition. Physicians can view CED maps updated at different time points along the patient's journey, thus observing acute effects such as changes in whether a medication is being administered, and chronic effects such as slow decline overtime. This presentation of additional data can help the physician make treatment decisions as well as communicate with the patient. This same data and displays can be shown to the patient in a more simplified manner to help them understand their progression overtime. Additionally, this same data can be analyzed to recognize patient trends and better advise treatment decisions.

An example provides automated scheduling recommendations. In the case that a patient demonstrates significant changes in CED because of medication state, time of day, or another repeated factor that repeats regularly, an optimizer could identify the pattern of shifting efficacy and propose/automate changes in stimulation (sometimes called "scheduling") to attempt to mitigate shifts in CED and maintain a patient within an anticipated target zone. For example, this may be performed by collecting CED regularly on PD relevant symptoms and showing a trend associated with the timing of medication. This trend is such that during periods of high medication state, less stimulation (or a different electrode configuration) is most effective. Based on the patient's known medication schedule, a stimulation schedule would be proposed that would maintain the patient in a more ideal stimulation state. An ideal stimulation state would be to maintain the patient's recordable CED within a set range (such as within the error bars of the CED). If CED drifts outside of the ideal range it would be marked as a significant change in patient state.

The present subject matter may be used when the patient is home. An example provides automated stimulation adjustments from shifting CED. An algorithm can review the shifted CED and propose a new stimulation setting better suited to the patient's present state. U.S. patent application Ser. No. 17/649,504, filed Jan. 31, 2022 and entitled "Automated Selection of Electrodes and Stimulation Parameters in a Deep Brain Stimulation System Employing Directional Leads", which is herein incorporated by reference in its entirety, provides an example of a programming algorithm that uses CED. The algorithm may look at all things tested and determines what should be tested next as part of a process to titrate or optimize therapy settings.

For example, in the state previously mentioned where bradykinesia and tremor are both improving in response to a maximal medication state, the algorithm may review the altered CED data and may increase the weight on the tremor signal to target stimulation preferentially at the clinical response that is less responsive to medication. The predicted stimulation change may be confined to settings previously tested in clinic or may be prioritized based on the stimulation configuration that would result in a smaller shift of the stimulation field. The new stimulation configuration may be automatically pushed to the stimulator. Physician or patient approval may be required prior to being pushed to the stimulator. Furthermore, the system may intelligently ramp from one configuration to another.

Automated scheduling adjustments may be provided. A goal of CED capture at home may be to maintain collected CED within a target state (such as that defined by the error bars). If a stimulation schedule is established, the system may attempt to predict a drift in CED outside of the target state based on a known event, such as the timing of medication. If an optimizer notes that the CED has a predictable drift outside of the target, the system may further modify and optimize the scheduling. For example, an optimizer may initially propose a schedule that begins changing stimulation twenty minutes after a patient has taken their medication. However, the optimizer notes that for the first ten minutes following stimulation change, the CED is out of range. The optimizer may shift the schedule slightly, so stimulation change occurs twenty-five minutes after a patient has taken their medication. This may result in significantly less CED outside of the target range.

Figure 13:
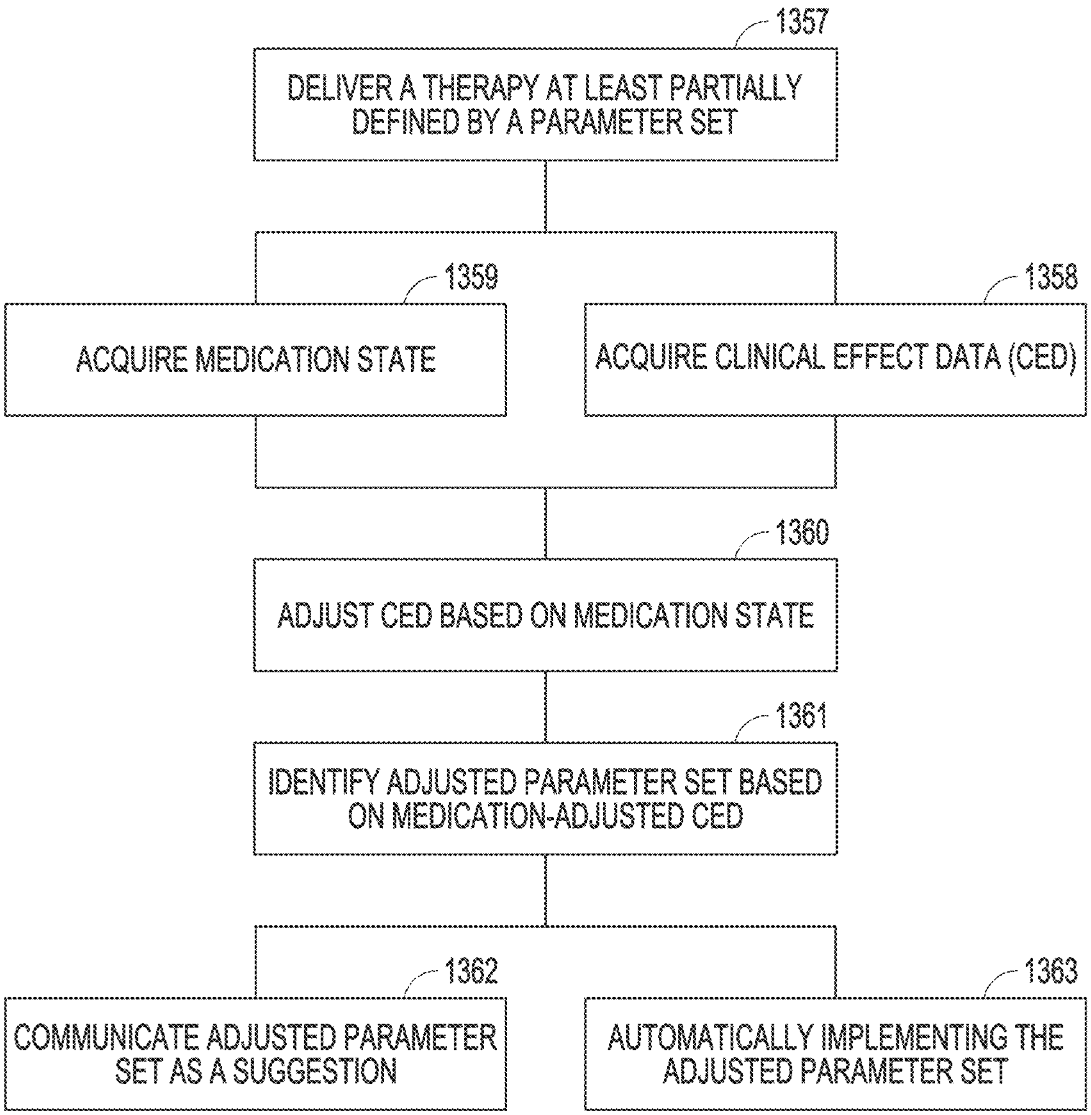
FIG. 13 illustrates, by way of example and not limitation, a method for using medication state and CED to determine updated therapy settings.

Steps may be taken to minimize the patient's perception of change when stimulation configurations are changed. The following examples are not intended to be limit the present subject matter. If an amplitude is being changed, the amplitude may be slowly decreased over a set span of time at small intervals until the target amplitude is reached. If the configuration of anodes and cathodes is changing, anodic and cathodic current may be slowly added to new contacts while being subtracted from the old contacts. If pulse width is changed then amplitude may be maintained or decrease so that the predicted change in volume of tissue activated would happen gradually. If a frequency or irregular stimulation pattern change is made, then compatible frequencies may be stepped through until the desired frequency is achieved. If multiple changes are required at once, the overall goal may be to shift the volume of tissue activated slowly in a way consistent with maintaining treatment delivery FIG. 13 illustrates, by way of example and not limitation, a method for using medication state and CED to determine updated therapy settings. A medical device may be used to treat a condition by delivering a therapy at least partially defined using a parameter set 1357. A processing system, which may but is not necessarily part of the medical device, may be used to acquire clinical effect data (CED) for the condition 1358, acquire a medication state of medication administered to treat the condition 1359, adjust (or update or estimate) the CED based on the medication state to provide medication-adjusted CED 1360, and identify an adjusted parameter set for the medical device to deliver the therapy based on the medication-adjusted CED 1361. The processing system may communicate the adjusted parameter set to a clinician as a suggestion 1362 and/or automatically implementing the adjusted parameter set 1363. Rather than or in addition to determining adjusted parameter sets, the system may be configured for use to compare medication-adjusted CEDs for different medication states, such as may be useful to adjust the medication dosing schedule.

The adjusted parameter set may be identified based on a comparison of a current medication-adjusted CED to a previous medication-adjusted CED. The medication state for at least one medicine may be determined using at least one sensor to determine the medication state by detecting a concentration of the medication in the patient, or by estimating the medication state based on at least one of: a medication schedule; the medication, the dose of the medication, and user input indicating a time when medication is administered; a characteristic shift in the treated condition, wherein the characteristic shift is determined using at least one of a sensor of the treated condition or a user input indicative of the treated condition; or at least one sensor configured to detect a characteristic shift in a physiological parameter.

The therapy may include DBS to treat Parkinson's Disease (PD). An accelerometer may be used to detect the CED (including data indicative of movement disorder). Movement disorders may include, but are not limited to, tremor, bradykinesia, dyskinesia, gait and balance problems, rigidity, tics, and the like. Other symptoms may include, by way of example and not limitation, muscle cramping, drooling, festination, freezing, soft speech. The therapy may include a neurostimulation therapy to treat pain. The CED for the therapy may be acquired using at least one of patient feedback or sensed data regarding pain (e.g., posture, facial recognition, heart rate, and the like). The therapy may include electrical stimulation for a cardiovascular therapy. The CED for the therapy may be acquired using at least one of blood pressure or cardiac activity such and heart rate and cardiac rhythm. Adjustments to a neuromodulation therapy, for example, may include, but are not limited to, one or more of a pulse amplitude, a pulse width, a pulse frequency, a pulse train duration, a pulse-to-pulse duty cycle, a pulse train to pulse train duty cycle, a stimulation schedule. active electrodes; or electrode fractionalization.

The CED may be acquired from previously collected data retrieved from storage. The medication state may be acquired using a medication schedule, user-inputted data indicating a time when medication was administered, or sensor data. The medication state may be a dimension in a CED vector or matrix used by an optimizer to determine the adjusted parameter set.

The therapy may be delivered within a therapy space defined by different parameters sets, where each of the different parameters sets defines values for a plurality of therapy parameters. The different parameter sets may include a first group for calibration and a second group. CED may be captured for the first group within the therapy space by delivering the therapy using each of the different parameter sets within the first group, capturing the CED for each of the different parameter sets, and adjusting the captured CED based on the medication state to provide medication-adjusted captured CED for each of the different parameter sets in the first group. The captured CED for the first group may be used to determine a prediction map to estimate medication-adjusted CED for different parameter sets within the second group. For example, modeling, which may be based on data from other patients, may to estimate medication-adjusted CED for different parameter sets within the second group.

Figure 14:
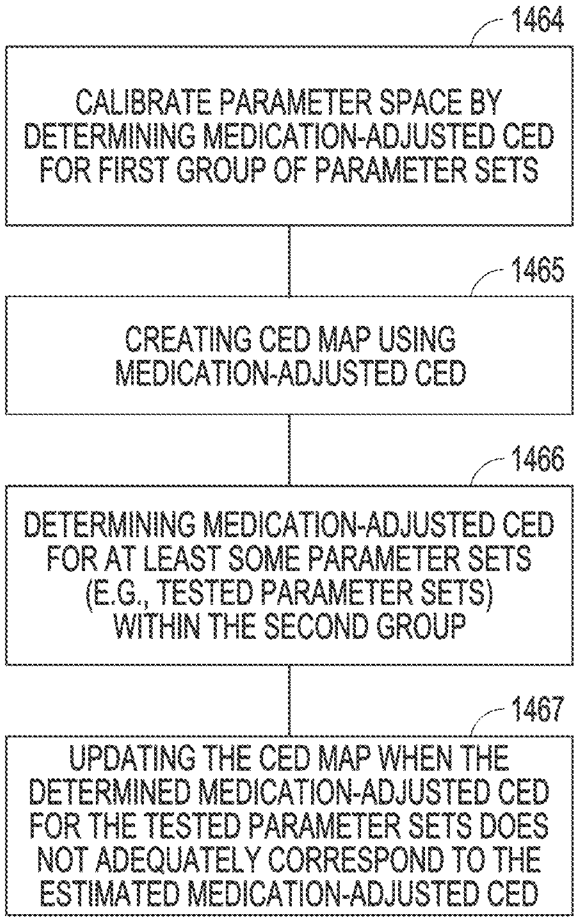
FIG. 14 illustrates, by way of example and not limitation, the updating of a CED map, which may include both captured and estimated CED.

FIG. 14 illustrates, by way of example and not limitation, the updating of a CED map, which may include both captured and estimated CED. The prediction map may be updated if a subsequently captured CED is outside of an acceptable error for a previously estimated CED or for a previously captured CED. A search space, or parameter space, may be calibrated by determining medication-adjusted CED for a first group of parameter sets 1464. A CED map may be created using medicated-adjusted CED for the first group to estimate medication-adjusted CED for a second group of parameter sets 1465. The medication-adjusted CED may be determined for at least some parameter sets within the second group 1466 which were previously estimated. The CED map may be updated when the determined medication-adjusted CED for the tested parameter sets does not adequately correspond to the estimated medication-adjusted CED 1467. Estimated CEDs may be associated with a confidence level in the accuracy of the estimation, and may be tested to verify the estimation based on a confidence level for the estimated CED. CED maps may be created for a plurality of times to map the medication-adjusted CED to the parameter set at each of the plurality of times. The CED maps may be displayed to a clinician or a patient.

Figure 15:
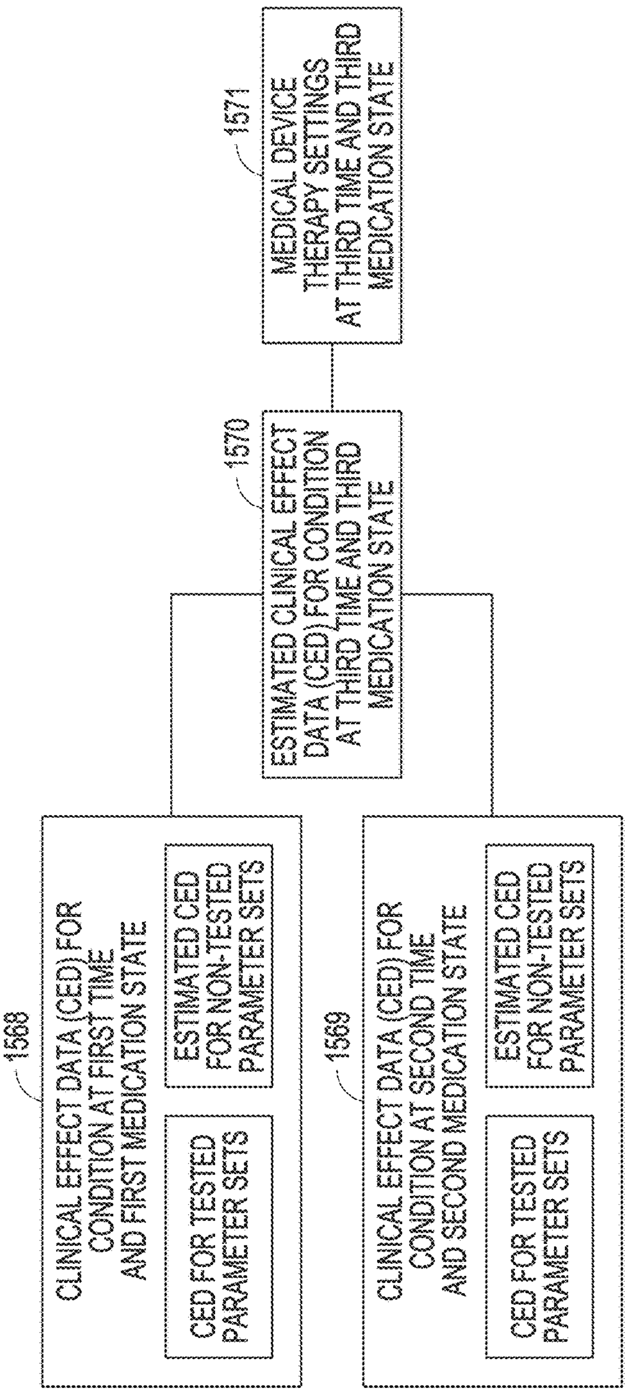
FIG. 15 illustrates, by way of example and not limitation, a method for estimating a medication-adjusted CED.

FIG. 15 illustrates, by way of example and not limitation, a method for estimating a medication-adjusted CED. First CED may be acquired for the condition at a first medication state 1568. Second CED may be acquired for a second medication state 1569. The acquisition of the first CED may include testing some parameter sets to capture CED and may include estimating CED for non-tested parameter sets. The second CED may be acquired by estimating medication-adjusted CED based on the first CED data, or may include testing some parameter sets to capture CED and may include estimating CED for non-tested parameter sets. Third CED for a third medication state or third time may be estimated based on the first and medication-adjusted CED 1570. Medical device therapy settings may be determined for the third time at the third medication state 1571.

Figure 16:
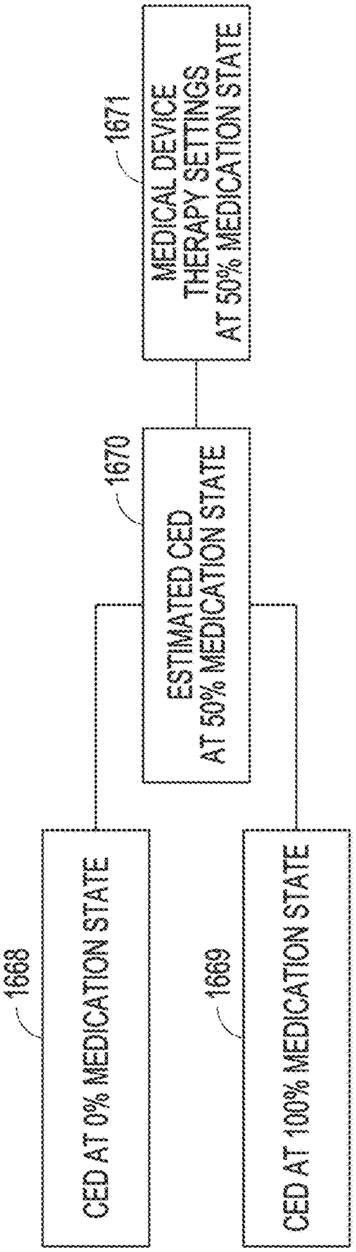
FIG. 16 illustrates, by way of example and not limitation, a specific example to illustrate the method shown in FIG. 15.

FIG. 16 illustrates, by way of example and not limitation, a specific example to illustrate the method shown in FIG. 15. A patient may have CED measured first in a complete medication off state (0%) 1668 and in a full medication on state (100%) 1669. As a practical matter, a clinician may only measure about thirty stimulation settings while the visible "map" of possible stimulation settings may be in the thousands or more. For those settings that were not tested, the value of the untested points in the stimulation space may be predicted using inverse distance weighting. Thus, there are two complete stimulation (CED) maps composed of tested and predicted values one in a med off 0% and one in a full 100% med on state. If a patient is, or is estimated to be, in a 50% on med state, their data may be predicted to fall between the 0% and 100% data. The translated 50% stimulation (CED) map may be estimated 1670. This estimation may be based on observations from other patients. This estimation may be confirmed by doing a limited number of stimulation tests to verify the predicted 50% stimulation (CED) map and updating the map as needed. Alternatively, if there is high confidence in the 50% stimulation (CED) map based on prior studies, the confirmation step may be bypassed. CED may only be collected for two medication states, and then other medication states may be estimated. Medical device therapy settings may be determined for the estimated 50% medication state 1671. The ON/OFF medication states are a relatively simple example. Those of ordinary skill in the art will understand, upon reading and comprehending this disclosure, that other more complex estimations may be made from one or more medication states and model(s) relating CED to medication states.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encrypted with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks or cassettes, removable optical disks (e.g., compact disks and digital video disks), memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A method, comprising using a medical device configured to treat a condition by delivering a therapy within a therapy space defined by different parameter sets, wherein the medical device includes a plurality of electrodes available for use to deliver electrical stimulation, the therapy space includes different combinations of electrode configuration parameters and pulse parameters for the electrical stimulation, and the therapy is at least partially defined using a parameter set selected from the different parameter sets; and using a processing system operatively connected to the medical device to:

acquire clinical effect data (CED) for the condition by testing a subset of the different parameter sets within the therapy space;

acquire a medication state of medication administered to treat the condition;

computationally adjust the CED acquired from the tested subset of parameter sets based on the medication state to provide medication-adjusted CED by executing a predictive algorithm that translates the CED to compensate for the medication effects on the condition, wherein the medication-adjusted CED includes transformed CED values that account for medication effects to enable comparison of CED across different medication states and estimation of CED for untested parameter sets within the therapy space;

identify an adjusted parameter set selected from the different parameter sets within the therapy space, the adjusted parameter set defining a combination of electrode configuration parameters and pulse parameters for the electrical stimulation, for the medical device to deliver the therapy based on the medication-adjusted CED by using the processing system to search the therapy space through evaluation of the medication-adjusted CED to select the adjusted parameter set; and cause the medical device to deliver the therapy using the adjusted parameter set to treat the condition by delivering the electrical stimulation through the plurality of electrodes according to the combination of electrode configuration parameters and pulse parameters defined by the adjusted parameter set.

2. The method of claim 1, wherein the adjusted parameter set is identified based on a comparison of a current medication-adjusted CED to a previous medication-adjusted CED.

3. The method of claim 1, further comprising determining the medication state for at least one medicine by:

using at least one sensor to determine the medication state by detecting a concentration of the medication in the patient; or estimating the medication state based on at least one of:

a medication schedule;

the medication, a dose of the medication, and user input indicating a time when medication is administered;

a characteristic shift in the treated condition, wherein the characteristic shift is determined using at least one of a sensor of the treated condition or a user input indicative of the treated condition; or at least one sensor configured to detect a characteristic shift in a physiological parameter.

4. The method of claim 3, wherein the therapy includes deep brain stimulation (DBS) to treat Parkinson's Disease (PD), the method further comprising using an accelerometer to detect the CED, wherein the CED includes data indicative of movement disorder.

5. The method of claim 3, wherein the therapy includes a neurostimulation therapy to treat pain, the method further comprising using at least one of patient feedback or sensed data regarding pain to detect the CED for the neurostimulation therapy.

6. The method of claim 3, wherein the therapy includes electrical stimulation for a cardiovascular therapy, the method further comprising using at least one of blood pressure or cardiac activity to detect the CED for the cardiovascular therapy.

7. The method of claim 1, wherein the therapy includes an electrical therapy, and the adjusted parameter set includes an adjustment to at least one of:

a pulse amplitude;

a pulse width;

a pulse frequency;

a pulse train duration;

a pulse-to-pulse duty cycle;

a pulse train to pulse train duty cycle;

a stimulation schedule;

active electrodes; or electrode fractionalization.

8. The method of claim 1, wherein the acquired CED includes previously collected data retrieved from storage, and the medication state is acquired using a medication schedule;

user-inputted data indicating a time when medication was administered, or sensor data.

9. The method of claim 1, further comprising including the medication state as a dimension in a CED vector or matrix used by an optimizer to determine the adjusted parameter set.

10. The method of claim 1, wherein:

the tested subset of the different parameter sets includes a first group for calibration and the untested parameter sets include a second group of different parameter sets, wherein computationally adjusting the CED acquired from the tested subset includes adjusting the CED for each of the different parameter sets in the first group based on the medication state to provide medication-adjusted captured CED that enables the estimation of CED for the second group of different parameter sets.

11. The method of claim 10, wherein estimating CED for the second group comprises generating a predictive map that interpolates or extrapolates CED values for individual parameter sets within the second group based on the medication-adjusted captured CED for the first group.

12. The method of claim 11, further comprising using data from other patients to estimate medication-adjusted CED for different parameter sets within the second group.

13. The method of claim 11, further comprising using the processing system to associate the captured and estimated CED with an acceptable error based on an anticipated error rate, capture CED for at least one parameter set which was previously estimated in the second group and determine the captured CED is outside of the acceptable error and respond by updating the prediction map.

14. The method of claim 13, further comprising assigning a confidence level to parameter sets within the second group based on an accuracy of estimation for the captured CED for the at least one parameter set in the second group, and testing other parameter sets in the second group based in the assigned confidence level.

15. The method of claim 1, wherein the adjusted parameter set maintains a set range by accounting for fluctuations in the medication state attributable to an absorption rate and clearance rate of the medication administered to treat the condition.

16. The method of claim 1, further comprising using the processing system to gradually ramp from the parameter set used to deliver the therapy to the adjusted parameter set.

17. The method of claim 1, further comprising creating CED maps at a plurality of times to map the medication-adjusted CED to the parameter set at each of the plurality of times, and displaying the CED maps to a clinician or a patient.

18. A method, comprising using a medical device configured to treat a condition by delivering a therapy within a therapy space defined by different parameter sets, wherein the medical device includes a plurality of electrodes available for use to deliver electrical stimulation, the therapy space includes different combinations of electrode configuration parameters and pulse parameters for the electrical stimulation, and the therapy is at least partially defined using a parameter set selected from the different parameter sets; and using a processing system operatively connected to the medical device to:

acquire first clinical effect data (CED) for the condition at a first medication state by testing one or more parameter sets within the therapy space;

acquire second CED for the condition at a second medication state by testing one or more parameter sets within the therapy space;

computationally estimate third CED for the condition at a third medication state using the first CED and the second CED by executing a predictive algorithm that translates CED values to compensate for medication effects on the condition, and the third CED includes estimated CED values that account for the third medication state to enable comparison of CED across the first, second, and third medication states;

identify an adjusted parameter set selected from the different parameter sets within the therapy space, the adjusted parameter set defining a combination of electrode configuration parameters and pulse parameters for the electrical stimulation for the medical device to deliver the therapy based on the third CED by using the processing system to search the therapy space through evaluation of the third CED to select the adjusted parameter set; and cause the medical device to deliver the therapy using the adjusted parameter set to treat the condition by delivering the electrical stimulation through the plurality of electrodes according to the combination of electrode configuration parameters and pulse parameters defined by the adjusted parameter set.

19. The method of claim 18, wherein the acquired first CED includes CED for tested parameter sets and estimated CED for non-tested parameters, or the processing system is configured to verify the estimated third CED by testing at least some parameter sets.

20. A system, comprising:

at least one medical device configured to treat a condition by delivering a therapy to a patient within a therapy space defined by different parameter sets, wherein the medical device includes a neurostimulator having a plurality of electrodes for delivering electrical stimulation, the therapy space includes combinations of electrode selection parameters and pulse parameters, and the therapy is at least partially defined using a parameter set selected from the different parameter sets;

a processing system operatively connected to the at least one medical device and configured for use to:

acquire clinical effect data (CED) for the condition by testing a subset of the different parameter sets within the therapy space;

acquire a medication state of medication administered to treat the condition;

computationally adjust the CED acquired from the tested subset of parameter sets based on the medication state to provide medication-adjusted CED by applying a computational model that translates CED values between medication states, wherein the computational model generates a predictive map from the tested subset that estimates CED for untested parameter sets, the predictive map is adjustable based on subsequently tested parameter sets, and the medication-adjusted CED includes transformed CED values that account for medication effects to enable comparison of CED across different medication states and estimation of CED for untested parameter sets within the therapy space;

identify an adjusted parameter set selected from the different parameter sets within the therapy space, the adjusted parameter set defining a combination of electrode configuration parameters and pulse parameters for the electrical stimulation for the at least one medical device to deliver the therapy based on the medication-adjusted CED; and cause the at least one medical device to deliver the therapy using the adjusted parameter set to treat the condition by delivering the electrical stimulation through the plurality of electrodes according to the combination of electrode selection parameters and pulse parameters defined by the adjusted parameter set.

* * * * *